US005804566A

United States Patent [19]
Carson et al.

[11] Patent Number: 5,804,566
[45] Date of Patent: Sep. 8, 1998

[54] METHODS AND DEVICES FOR IMMUNIZING A HOST THROUGH ADMINISTRATION OF NAKED POLYNUCLEOTIDES WITH ENCODE ALLERGENIC PEPTIDES

[75] Inventors: Dennis A. Carson, Del Mar; Eyal Raz, San Diego, both of Calif.; Meredith L. Howell, Corvallis, Oreg.

[73] Assignee: The Regents of the University of California, Alameda, Calif.

[21] Appl. No.: 333,068

[22] Filed: Nov. 1, 1994

Related U.S. Application Data

[63] Continuation-in-part of Ser. No. 112,440, Aug. 26, 1993, abandoned.

[51] Int. Cl.[6] .......................... A61K 48/00; C12N 15/12; C12N 15/52
[52] U.S. Cl. ........................ 514/44; 536/23.1; 424/184.1
[58] Field of Search ............................. 514/44; 536/23.1; 424/184.1

[56] References Cited

U.S. PATENT DOCUMENTS 5,580,859 12/1996 Felgner et al. ............................. 514/44
5,589,466 12/1996 Felgner et al. ............................. 514/44

FOREIGN PATENT DOCUMENTS

WO 90/11092 10/1990 WIPO .

OTHER PUBLICATIONS

Mader et al., PNAS, 1993, 90:5603.
Chien, "Mucosal Drug Delivery: Potential Routes for Noninvasive Systemic Administration," *Novel Drug Delivery Systems,* vol. 50, pp. 197–227.
Chien, "Transdermal Drug Delivery and Delivery Systems," *Novel Drug Delivery Systems,* vol. 50, pp. 301–380.
Chien, "Nasal Drug Delivery and Delivery Systems," *Novel Drug Delivery Systems,* vol. 50, pp. 229–268.
Sloan, "Use of Solubility Parameters from Regular Solution Theory to Describe Partitioning–Driven Processes," *Prodrugs: Topical and Ocular Drug Delivery,* vol. 53, pp. 179–204.
Tice, et al., "Parenteral Drug Delivery: Injectables," *Treatise on Controlled Drug Delivery,* pp. 315–339.
Chang, et al., "Nasal Drug Delivery," *Treatise on Controlled Drug Delivery,* pp. 423–463.
Been, et al., "One Binding Site Determines Sequence Specificity of Tetrahymena Pre–rRNA Self Splicing, Trans–Splicing, and RNA Enzyme Activity," *Cell,* vol. 47, 207–216, Oct. 24, 1986.
Gillies, et al., "Expression of Human Anti–Tetanus Toxoid Antibody in Transfected Murine Myeloma Cells," *Bio/Technology,* vol. 7, Aug. 1989, pp. 799–804.
Ward, et al., Binding activities of a repertoire of single immunoglobulin variable domains secreted from *Escherichia coli, Nature,* vol. 341, 12 Oct. 1989, pp. 544–546.

Wolff, et al., Conditions Affecting Direct Gene Transfer into Rodent Muscle In Vivo, *BioTechniques* vol. 11, No. 4 (1991), pp. 474–485.
Cohen, "Naked DNA Points Way to Vaccines," *Science,* vol. 259, 19 Mar. 1993, pp. 1691–1692.
Acsadi, et al., "Human dystrophin expression in mdx mice after intramusclular injection of DNA constructs," *Nature,* vol. 352, 29 Aug. 1991, pp. 815–818.
Wolff, et al., "Indirect Gene Transfer into Mouse Muscle in Vivo," *Science,* vol. 24, Mar. 1990, pp. 1465–1468.
Barr, et al., "Systemic Delivery of Recombinant Proteins by Genetically Modified Myoblasts," *Science,* vol. 254, Dec. 1991, pp. 1507–1512.
Ulmer, et al., "Heterologous Protection Against Influenza by Injection of DNA Encoding a Viral Protein," *Science,* vol. 259, 19 Mar. 1993, pp. 1745–1748.
"The Ultimate Delivery System: Lectro Patch Instructions," Advertisement by General Medical Company.
Kaplan, et al., "Rational Immunotheraphy with Interleukin 2," *Bio/Technology,* vol. 10, Feb. 1992, pp. 157–162.
Caligiuri, et al., "Selective Modulation of Human Natural Killer Cells In Vivo After Prolonged Infusion of Low Dose Recombinant Interleukin 2," *J. Clin. Invest.,* vol. 91, Jan. 1993, pp. 123–132.
Teppler, et al., "Prolonged Immunostimulatory Effect of Low–Dose Polyethylene Glycol Interleukin 2 in Patients with Human Immunodeficiency Virus Type 1 Infection," *J. Exp. Med.,* vol. 177, Feb. 1993, 483–492.
Lotz, et al., Brief Definitive Report, *J. Exp. Med.,* vol. 67, Mar. 1988, 1253–1258.
Robinson, et al., "Use of Direct DNA Inoculations to Elicit Protective Immune Responese," *Journal of Cellular Biochemistry,* Supp. 17D, 1993, p. 92.
Donohue, et al., "In Vivo Administration of Purified Jurkat–derived Interleukin 2 in Mice," *Cancer Research,* vol. 44, Apr. 1984, pp. 1380–1386.
Goldstein, et al., "Repetitive Weekly Cycles of Interleukin 2: Effect of Outpatient Treatment with a Lower Dose of Interleukin 2 . . . ," *Cancer Research,* vol. 49, pp. 6832–6839, Dec. 1, 1989.

(List continued on next page.)

*Primary Examiner*—Frank C. Eisenchenck
*Attorney, Agent, or Firm*—Fish & Richardson P.C.

[57] ABSTRACT

The invention is directed to methods for introducing biologically active peptides into a host by administration of polynucleotides which operatively encode for the peptide of interest. In a preferred embodiment of the invention, a mammal is desensitized to an antigen, in particular an allergen, through administration to the mammal of polynucleotides which operatively encode the antigen. The antigen-encoding polynucleotides are administered to host tissues which have a high concentration of antigen presenting cells in them relative to other host tissues. The method is particularly useful in treating allergies because the allergen-encoding polynucleotides of the invention to induce tolerance while suppressing IgE antibody formation. Devices and compositions for use in the methods of the invention are also described.

10 Claims, 20 Drawing Sheets

OTHER PUBLICATIONS

Hefeneider, et al., "In Vivo Interleukin 2 Administration Augments the Generation of Alloreactive Cytolytic T Lymphocytes and Resident Natural Killer Cells," *Journal of Immunlogy,* vol. 130, No. 1, 1/83, 222/227.

Stribling, et al., "Aerosol gene delivery in vivo," *Proc. Natl. Acad. Sci. USA,* vol. 89, pp. 11277–11281 Dec. 1992.

Del Rey, et al., "Antidiabetic effects of interleukin 1," *Proc. Natl. Acad. Sci. USA,* vol. 86, pp. 5943–5947, Aug. 1989.

Shields, et al., "Calorie restriction suppresses subgenomic mink cytopathic focus–forming murine leukemia virus transcription and frequency . . . ," *Proc. Natl. Acad. Sci. USA,* vol. 88, pp. 11138–11142, Dec. 1991.

Tang, et al., "Genetic immunization is a simple method for eliciting an immune response," *Nature,* vol. 356, 12 Mar. 1992, pp. 152–154.

Gorman, et al., "The Rous sarcoma virus long terminal repeat is a strong promoter when introduced into a variety of eukaryotic cells . . . ," *Proc. Natl. Acad. Sci. USA,* vol. 79, pp. 6777–6781, Nov. 1982.

Norton, et al., "Bacterial B–Galactosidase as a Marker of Rous Sarcoma Virus Gene Expression and Replication," *Molecular and Cellular Biology,* vol. 5, No. 2, Feb. 1985, pp. 281–290.

Krieg, et al., "Functional messenger RNAs are produced by SP6 in vitro transcription of cloned cDNAs," Nucleic Acids Research, IRL Press Limited, vol. 12, No. 18, 1984, pp. 7057–7070.

*Multi–Test,* Lincoln Diagnostics, Inc., pp. 1–6.

Terr, "Allergy Desensitization," pp. 739–743.

Secrist, et al., "Allergen Immunotherapy Decreases Interleukin 4 Production in CD4+ T Cells from Allergic Individuals," *J. Exp. Med.,* vol. 178, Dec. 1993, pp. 2123–2130.

Kemeny, et al., "CD8+ T cells in allergy," *Allergy,* 47:12–21, 1992.

Nakagawa, et al., "Immunotherapy of Allergic Diseases," *Int. Arch. Allergy Immunol.,* 102:117–120 (1993).

Chua, et al., "Sequence Analysis of cDNA Coding for a Major House Dust Mite Allergen," *J. Exp. Med.,* vol. 167, Jan. 1988, pp. 175–182.

Davis, et al., "Plasmed DNA Is Superior to Viral Vectors for Direct Gene Transfer into Adult Mouse Skeletal Muscle," *Human Gene Therapy,* 4:733–740 (1993).

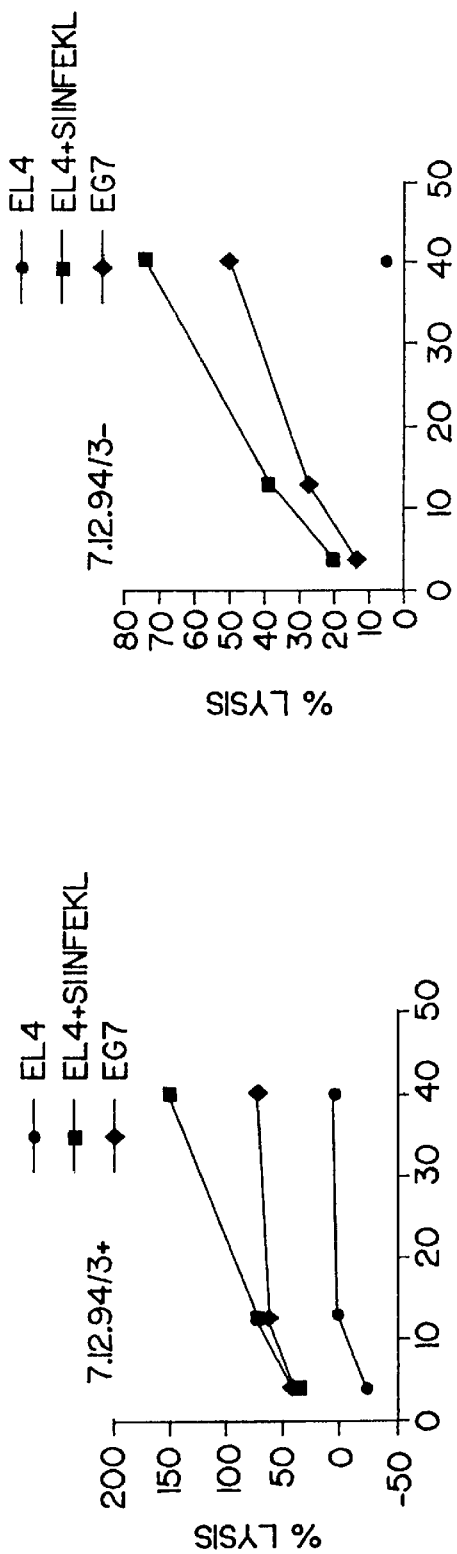
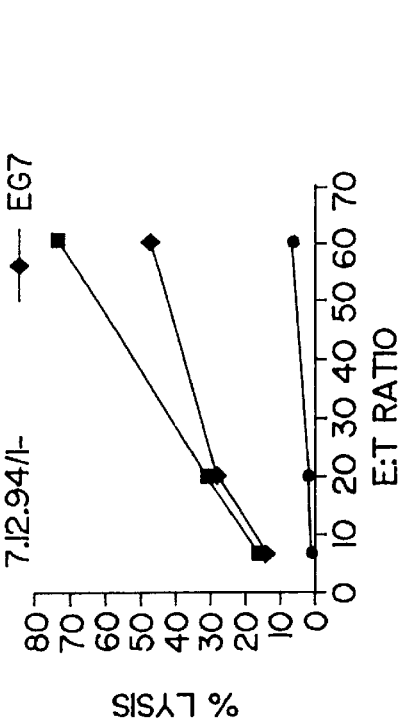
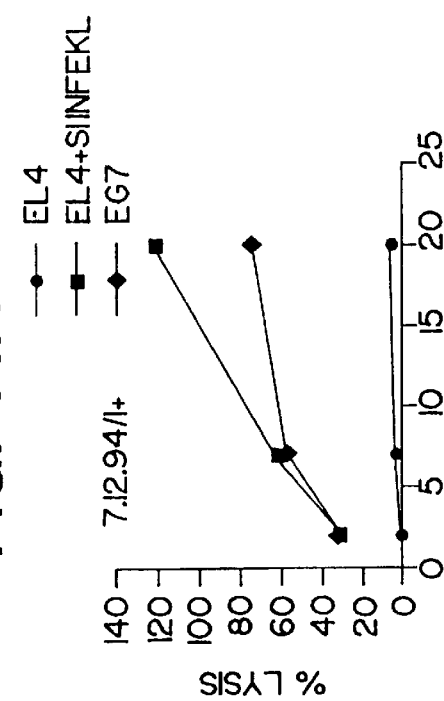
FIG. 11A, FIG. 11B, FIG. 11C, FIG. 11D

METHODS AND DEVICES FOR IMMUNIZING A HOST THROUGH ADMINISTRATION OF NAKED POLYNUCLEOTIDES WITH ENCODE ALLERGENIC PEPTIDES

RELATED PATENT APPLICATIONS

This is a continuation-in-part of PCT Application No. US94/09661, filed Aug. 25, 1994 (designating the U.S. as an elected state), which is in turn a continuation-in-part of U.S. Ser. No. 08/112,440, filed in the United States Patent and Trademark Office on Aug. 26, 1993, now abandoned.

STATEMENT OF GOVERNMENT RIGHTS

This invention may have been made with Government support under Grant Nos. AR07567 and AR25443, awarded by the National Institutes of Health. The Government may have certain rights in this invention.

BACKGROUND OF THE INVENTION

1. Field of the Invention

This invention relates to methods for administering biologically active peptides to a mammalian host by the introduction thereto of one or more polynucleotides to operatively encode for the peptides, preferably by non-invasive means. It also relates to the administration of said polynucleotides to immunize a host against one or more antigens. In particular, the invention relates to the immunization of a host against one or more allergens for treatment of allergy.

2. Description of Related Art

The direct introduction of a biologically active peptide or protein into the cells of a patient can have significant therapeutic value. However, this approach also has several drawbacks. Of primary concern is the risk of potential toxicities, particularly at dosages sufficient to produce a biological response to the peptide. From a practical perspective, there is also the problem of the cost associated with isolating and purifying or synthesizing the peptides. Moreover, the clinical impact of the peptides is also limited by their relatively short half-life in vivo which usually results from their degradation by any proteases present in the target tissue.

For these reasons, introduction of a protein into a patient by delivery of a gene which will express the protein in the patient/host is an intriguing alternative to administering the protein.

In 1984, work at the NIH was reported which showed that intrahepatic injection of naked, cloned plasmid DNA for squirrel hepatitis into squirrels produced both viral infection and the formation of antiviral antibodies in the squirrels (Seeger, et al., *Proc. Nat'l. Acad. Sci USA*, 81:5849–5852, 1984). Several years later, Feigner, et al., reported that they obtained expression of protein from "naked" polynucleotides (i.e., DNA or RNA not associated with liposomes or a viral expression vector) injected into skeletal muscle tissue (Feigner, et al., *Science*, 247:1465, 1990; see also, PCT application WO 90/11092). Feigner, et al. surmised that muscle cells efficiently take up and express polynucleotides because of the unique structure of muscle tissue, which is comprised of multinucleated cells, sarcoplasmic reticulum and a transverse tubular system which extends deep into the muscle cell.

Although it has been supposed that cells of other tissues may also be able to take up naked polynucleotides, expression in other tissues has only been identified to date when delivery of the expressed gene was via a delivery system, e.g., liposomal transformation of the cells. Indeed, other researchers have suggested that uptake and expression of naked polynucleotides in tissues other than skeletal muscle does not occur at detectable or biologically active levels (see, e.g., Stribling, et al., *Proc. Natl. Acad. Sci. USA*, 89:11277–11281, 1992 [expression following aerosol delivery of a gene occurred with use of a liposomal delivery system but not with introduction of DNA alone]; and, Tang, et al., *Nature*, 356:152–154,1992 [injection with a vaccine "gun" of an hGH plasmid coupled to colloidal gold beads]).

Although generally effective for gene expression within muscle cells, injection of DNA or RNA into muscle tissue for long-term therapy requires use of repeated injections to offset loss of expression from gene degradation. This approach may not only be time-consuming and expensive, but may also be impractical due to inflammation caused at and near the site of injection. Such inflammation can cause muscle or other somatic cells into which nucleotides are introduced to be themselves targeted by an immune response (see, e.g., Example I) and can lead to severe myonecrosis. Further, intramuscular injection of DNA not only risks injury to muscle tissue, but that injury apparently also compromises the efficacy of the therapy. For example, researchers working with the University of Ottawa recently observed that "[s]triated muscle is the only tissue found to be capable of taking up and expressing reporter genes that are transferred in the form of plasmid DNA . . . but our findings indicate that fibers damaged by the injection procedure do not take up and express plasmid DNA." (Davis, et al., *Human Gene Therapy*, 4:151–159, 1993).

Further, while use of intramuscular injections may be effective on at least a short term basis in therapies directed to disease in the muscle tissue itself, it is likely to be less effective in stimulating a tissue specific immune or other biological response to the expressed peptide elsewhere in the patient's body. As a result, intramuscular injection is not a particularly viable route for achieving expression of peptides at the primary entry points for many infections; i.e., skin and mucosa.

Further, it appears that intramuscular injections of polynucleotides will lead to the formation of both antibodies and cytotoxic T cells in the tissue, due to release of any encoded protein by targeted muscle cells. In contrast, injection of protein (e.g., in a vaccination scheme) does not usually induce cytotoxic T cell formation because exogenous proteins do not efficiently enter the class I processing pathway.

In PCT application WO 90/11092 (discussed supra), the inventors propose that the injection of naked DNA into skeletal muscle or other somatic tissues will lead to direct gene expression in the cytoplasm of the injected cells. The inventors further suppose that the encoded protein will then enter the class I processing pathway to induce cytotoxic T cell formation (which are necessary for the control of established viral infections and cancers). However, as discussed above, it appears that instead any somatic cell that expresses antigen must first release the antigen into the extracellular space for uptake by antigen presenting cells before a class I restricted cytotoxic T cell response can to the antigen can be induced. This conclusion is supported by recent research regarding antigen presentation where the observation was made that "the priming of an immune response against . . . class I restricted antigen that is expressed exclusively in non-hematopoietic cells invovlves the transfer of that antigen to a host bone marrow derived cell before its presentation." (Huang, et al., *Science*, 264:961–965, 1994). Thus, at least one premise on which the method for introduction of genetic material into muscle cells for protein expression and immunization of PCT application WO 90/11092 was based may not be accurate.

Use of intramuscular injections can, however, produce relatively high levels of protein expression systemically prior to degradation of the injected gene. While this response is desirable in therapies where protein replacement is the goal, it can lead to unintended toxicities in immunization protocols where relatively rapid clearance or lower levels of expression are optimal. As a result, introduction of the gene into tissues which regularly shed or regenerate (such as skin) and/or into cells with a relatively high attrition rate in vivo (such as antigen presenting cells) would be more useful routes for gene immunization.

With respect to delivery systems for genes, means such as viral vectors which introduce the gene into the host's genome present potential health risks association with damage to the genetic material in the host cell. Use of cationic liposomes or a biolistic device (i.e., a vaccine "gun" which "shoots" polynucleotides coupled to beads into tissue) to deliver genes in vivo is preparation intensive and requires some experimentation to select proper particle sizes for transmission into target cells. Further, any invasive means of introducing nucleotides (e.g., injection) poses problems of tissue trauma (particularly in long-term therapies) and presents limited access to certain target tissues, such as organs.

Means for non-invasive delivery of pharmaceutical preparations of peptides, such as iontophoresis and other means for transdermal transmission, have at least the advantage of minimizing tissue trauma. However, it is believed that the bioavailability of peptides following transdermal or mucosal transmission is limited by the relatively high concentration of proteases in these tissues. Yet unfortunately, reliable means of delivering peptides (such as allergenic antigens) by transdermal or mucosal transmission of genes encoding for them has been unavailable.

The potential benefits of successful administration of peptides via in vivo expression of naked polynucleotides can be illustrated by comparison to the present state of allergen immunotherapy wherein allergenic extracts or purified allergens are administered to a patient to treat or prevent the occurrence of an allergic response to the allergen in the patient.

Conventional immunotherapy of allergic conditions seeks to desensitize the patient to an allergen and is most often used in the treatment and control of IgE antibody-mediated disease. Typically, the patient receives subcutaneous injections of sterile allergen extracts (usually crude or partially purified aqueous extracts of common allergens) once or twice a week until a dose is reached that will produce a transient area of inflammation at the site of injection, followed by regular maintenance doses of allergen.

The mechanism by which allergen immunotherapy desensitizes the patient to an allergen is not fully understood; however, it is probable that the therapy reduced the levels of production of IL-4 (which could otherwise stimulate production of IgE antibody) by CD4+ T cells (see, Secrist, et al., *J. Exp. Med.*, 178:2123–2129, 1993). It is also possible that allergen immunotherapy induces allergen-specific IgG blocking antibodies which may compete with IgE antibodies, thus preventing the release of mediators from mast cells (see, Nakagawa, et al., *Int. Arch. Allergy Immunol.*, 102:117–120, 1993). Researchers have also reported that allergen immunotherapy encourages activation of antigen-specific suppressor T cells, which may in turn induce anergy of TH2 lymphocytes (the T cells responsible for IgE antibody formation) (see, Tamir, et al., *J. Allergy Clin. Immunol.*, 79:591–598, 1987).

While relatively efficacious, allergen immunotherapy is not without criticism, principally because of the risk it poses of anaphylaxis and lesser related conditions, such as angioedema and asthma. The risk of adverse reactions is greatest in persons who are hypersensitive to particular allergens, but is present in all allergen immunotherapy patients due to the increase in IgE antibody production which is common during the early phases of treatment.

One trial approach to minimization of the risk of anaphylaxis employs peptide fragments of allergens (in particular, the cat allergen Fel dl) rather than whole allergens. The theory behind this approach is that the fragments will interact specifically with T cell epitopes, thus minimizing the risk of anaphylactic reactions (see, e.g., Romagnani, *Int. Arch. Allergy Immunol.*, 98:279–285, 1992). However, one drawback of peptide immunotherapy is the need to identify and isolate or synthesize peptides which will specifically bind to T cell epitopes. A need, therefore, exists for a relatively risk free allergy treatment which will suppress IgE production in toto without requiring specialized handling of proteinaceous allergens.

More generally, the above discussion also illustrates the need for an effective means of introducing naked nucleotides which will express in vivo a peptide which can induce local immunity in skin and mucosa to vaccinate a host against, for example, sexually transmitted diseases and respiratory illnesses. It also suggests a need for a means of introducing a gene encoding for a biologically active peptide to a host in a tissue-specific manner without significant tissue trauma.

The present invention addresses all of these needs.

SUMMARY OF THE INVENTION

The details of the preferred embodiment of the present invention are set forth in the accompanying drawings and the description below. Once the details of the invention are known, numerous additional innovations and changes will become obvious to one skilled in the art.

1. DEFINITIONS

The following definitions are provided to simplify discussion of the invention. Those skilled in the art will, however, recognize that these definitions may be expanded to include equivalents without departing from the legitimate scope or spirit of the invention. For this reason, these definitions should not be construed as limiting the invention.

a. "Naked polynucleotide(s)" refers to DNA or RNA and can include sense and antisense strands as appropriate to the goals of the therapy practiced according to the invention. Polynucleotide in this context may include oligonucleotides. Naked in this context means polynucleotides which are not complexed to colloidal materials (including liposomal preparations), or contained within a vector which would cause integration of the polynucleotide into the host genome.

b. "Operatively encoding" refers to a polynucleotide which has been modified to include promoter and other sequences necessary for expression and, where desired, secretion of the desired translation product; e.g., a peptide or protein. All the embodiments of the invention can be practiced using known plasmid expression vectors. Preferably, these vectors will include cDNA ('s) which encode for the desired translation product. Therefore, unless context otherwise requires, it will be assumed that "polynucleotide" or "naked polynucleotide" refers to operatively encoding sequences contained in a suitable plasmid expression vector, examples of which are provided herein.

c. "Mixture of polynucleotides" shall refer to more than one and up to 200 polynucleotide species which are under the control of the same promoter.

d. "Synthesis" refers to well-known means of synthesizing polynucleotide sequences and may include isolation and purification of native polynucleotides.

e. "Peptide" refers to small peptides, polypeptides, oligopeptides and proteins which have a desired biological effect in vivo.

f. "Iontophoresis" refers to a known means of transdermal transmission presently used to deliver peptides continuously to a host. More specifically, it is a process that facilitates the transport of ionic species by the application of a physiologically acceptable electrical current. This process and other transdermal transmission means are described in Chien, et al. *Transdermal Drug Delivery*, "Novel Drug Delivery Systems", Ch. 7, part C, (Marcel Dekker, 1992), the relevant disclosures of which are incorporated herein by this reference for the purpose of illustrating the state of knowledge in the art concerning techniques for drug delivery.

g. "Detergents/Absorption Promoters" refers to chemical agents which are presently known in the art to facilitate absorption and transfection of certain small molecules, as well as peptides.

h. "Antigen Presenting Cells", or "APC's" include known APC's such as Langerhans cells, veiled cells of afferent lymphatics, dendritic cells and interdigitating cells of lymphoid organs. The definition also includes mononuclear cells such as (1) lymphocytes and macrophages which take up and express polynucleotides according to the invention in skin and (2) mononuclear cells depicted on histological photographs contained herein. These cells are not tissue cells but are likely to be antigen presenting cells. The most important of these with respect to the present invention are those APC's which are known to be present in high numbers in epithelia and thymus dependent areas of the lymphoid tissues, including epidermis and the squamous mucosal epithelia of the buccal mucosa, vagina, cervix and esophagus (areas with "relatively high" concentrations of APC's). In addition to their definitions set forth below, therefore, "skin" and "mucosa" as used herein particularly refer to these sites of concentration of APC's.

i. "Host" refers to the recipient of the therapy to be practiced according to the invention. The host may be any vertebrate, but will preferably be a mammal. If a mammal, the host will preferably be a human, but may also be a domestic livestock or pet animal.

j. "Target tissue" refers to the tissue of the host in which expression of the naked polynucleotide is sought.

k. "Skin" as used herein refers to the epidermal, dermal and subcutaneous tissues of a host.

l. "Mucosa" refers to mucosal tissues of a host wherever they may be located in the body including, but not limited to, respiratory passages (including bronchial passages, lung epithelia and nasal epithelia), genital passages (including vaginal, penile and anal mucosa), urinary passages (e.g., urethra, bladder), the mouth, eyes and vocal cords.

m. "Point of Entry" refers to the site of introduction of the naked polynucleotide into a host, including immediately adjacent tissue.

n. "Dermal" and "Epidermal Administration" mean routes of administration which apply the naked polynucleotide(s) to or through skin. Dermal routes include intradermal and subcutaneous injections as well as transdermal transmission. Epidermal routes include any means of irritating the outermost layers of skin sufficiently to provoke an immune response to the irritant. The irritant may be a mechanical or chemical (preferably topical) agent.

o. "Epithelial Administration" involves essentially the same method as chemical epidermal administration, except that the chemical irritant is applied to mucosal epithelium.

p. "IL" refers to interleukin.

q. "TH1 Response(s)" refers to a cellular immune response that is induced preferentially by antigens that bind to and activate certain APC's; i.e., macrophages and dendritic cells.

r. "Biologically Active Peptide(s)" refers to a peptide which, when administered to a host, exerts a therapeutic benefit or induces an immune response therein.

s. "Activating Ligand" refers to a ligand which, when bound to a nuclear receptor, induces activity on the part of the receptor.

2. DISCUSSION

In one aspect, the invention consists of means of inducing local immunity to an antigen or a systemic response to a therapeutic peptide or polynucleotide by delivering a naked polynucleotide to a host's cells which operatively encodes the antigen or peptide. More particularly, the naked polynucleotide is preferably delivered to a tissue which contains a relatively high concentration of antigen presenting cells as compared to other tissues of the body. Although it is not intended that the invention will be entirely limited by a particular theory as to the mechanism of expression involved, it is believed that a biological response in these tissues following administration of the naked polynucleotide is achieved because the polynucleotide is expressed intracellulary in the cytoplasm of mononuclear cells, most likely the host's antigen presenting cells. It is also believed that the mononuclear cells may be involved in an inflammatory immune response to the naked polynucleotide once the cells have migrated into the lymph system and presented the expressed peptide as antigen.

Based on histological studies, the naked polynucleotides do not appear to be taken up directly by fibroblasts or other tissue cells in significant quantities (see, Example IV and FIG. 6). This conclusion is borne out by studies showing that (1) intradermal administration of even minute amounts of naked polynucleotides into mice induced a prominent TH1 response (indicative of antigen presentation by macrophages and dendritic cells; see, Example XI and XII, as well as FIGS. 15–19); (2) intradermal administration of naked polynucleotide to mice induced the formation of cytotoxic T cells without stimulating production of detectable levels of antibody (see, Example IX and FIGS. 11–12); and, (3) induction of prolonged immunological memory with respect to the polynucleotide expression product as an antigen (Example X and FIGS. 13–14). It therefore appears that the immunogeneity of naked polynucleotides depends not on the amount of protein expressed thereby, but instead on the type of cell transfected (e.g., antigen presenting cells versus tissue cells).

Given the apparent role of inflammation in this method of the invention, it will also be appreciated by those of skill in the art that increased permeability in cell membranes of the target tissue associated with inflammation may enhance uptake of the naked polynucleotides (particularly across barriers such as skin and mucosa).

Ideally, the target tissue will be skin or mucosa, where approximately 1% to 2% of the cell population is comprised of antigen presenting cells. These tissues are particularly preferred when the therapy is directed to infections or diseases where it is desirable to induce a localized therapeutic or immune response. For example, a mucosal route of administration would be preferred for treatment of sexually transmitted diseases, where the therapy was directed to boosting the immune response to antigens in infected tissues. A nasal route of administration (via inhalation or insufflation) would also be of particular use in therapies directed toward treatment of respiratory and related diseases. Further, a mucosal or dermal route would be useful in immunizing against allergens. These tissues are also preferred for their regenerative ability, which limits the length of time that introduced materials will remain at the point of entry.

Because the antigen presenting cells present in the target tissue may serve to mediate the expression of the naked polynucelotide, the method of the invention may not be as useful for inducing systemic responses to the expressed peptide as it is for inducing a localized response. However, at sufficient dosage levels a transitory systemic effect can be induced. A useful application of this aspect of the invention for induction of systemic responses to the expressed peptide may, therefore, be as an adjuvant for other systemic therapies.

In another aspect of the invention, the APC's serve as vehicles to deliver the naked polynucelotide to lymphatic organs and to mucosal tissues other than those at the point of entry. This embodiment is illustrated by reference to the following hypothesis; the mechanism described should not, however, be construed as limiting the invention.

In this embodiment, it is believed that the APC's take up the naked polynucelotide at or near the point of entry then carry them into lymphatic circulation. Once at a lymph node, the APC will present the intracellularly expressed protein as an antigen, thereby stimulating an immune response. From there, those APC's which carry "homing" receptors for, e.g., mucosa, may reenter lymphatic circulation until they settle in a target tissue other than the tissue at the point of entry. Where desired, homing receptors (specific membrane proteins which bind to target cell ligands) may be sequenced and incorporated into the naked polynucleotide.

With respect to expression in the lymph system, this embodiment also provides a means of enhancing the host's immune responsiveness by delivering cytokines to increase the concentration of specific cytokines present in the host. Particularly in the lymphatic organs, increases in the host's levels of circulating cytokines (administered with or shortly after antigen challenge) can boost the host's immune response to pathogenic antigens and (1) serve as an adjuvant for vaccines, (2) decrease the immune response to self-antigens in autoimmune diseases, or (3) decrease the immune response to alloantigens (produced, for example, following tissue or organ transplantation).

Another use for the invention would be in moderating an allergic response to an antigen by immunizing the host against the antigen. The skin and nasal routes of administration, particularly the former, are of particular use in this regard.

For example, genes for IL-2, gamma interferon and/or transforming growth factor (TGFβ) could be administered to suppress production of IgE molecules. This approach is of particular interest because, in recent clinical trials, IL-2 and gamma interferon have proved toxic at dosages sufficient to interfere with production of IgE. In addition, because IgE molecules are predominately present in skin and mucosa, use of these routes as points of entry according to the invention can be expected to be particularly effective in moderating allergic responses in these tissues.

Moreover, an unexpected discovery underlying the invention is that immunization of a host against an allergen with an allergen-encoding polynucleotide suppresses the IgE antibody response that is typically produced on immunization of a host with the allergen itself. In addition, allergen-specific cytotoxic T lymphocytes arise in hosts immunized with allergen-encoding polynucleotides in substantially greater volume than are produced on immunization with the allergen. Thus, the invention provides a more efficacious, less risk-intensive means of allergen immunotherapy than is presently available.

Further examples where it would be useful to induce a localized response in skin or mucosa are extant. In particular, a mucosal route of administration would be preferred for treatment of sexually transmitted diseases. The therapy can be directed toward modulating the local immune response to an infectious agent such as HIV, human papillomae viruses (such as those responsible for causing genital warts), or to cutanaceous viral infections. Also, where immunosuppresion is of therapeutic value, gene(s) operatively encoding for immunosuppressive agents (such as TGFβ) could also be supplied according to the method of the invention. An example where this approach would be useful is in the treatment of inflammatory bowel disease.

Another particular advantage of the invention is that it involves the administration of relatively minute doses of antigen. More specifically, because a polynucleotide that will operatively encode for an antigen is administered in lieu of the antigen itself, the quantity of foreign material being introduced to the host is relatively minimal. Moreover, routes of administration of naked polynucleotides through skin or mucosa require a lower concentration of DNA to produce the same magnitude of immune response than does the intramuscular route of administration (e.g., about 10–50 fold lower; see, e.g., Example 11 and FIGS. 13–14). As a result, the invention lends itself well to the administration of naked polynucleotides which encode for up to several hundred different antigens for use, as an example, as a polyvalent vaccine.

The preferred routes of administration for inducing local immunity in or near the skin will be by transdermal transmission, intradermal injection or superficially scratching or irritating the outermost layer of epidermal cells (i.e., epidermal administration), although subcutaneous injection may also be of use in certain applications. The preferred routes of administration for inducing local immunity in the respiratory tract will be by inhalation or insufflation; routes of administration to other mucosal tissues will vary according to their location.

Where the naked polynucleotides are to be introduced into skin or mucosa, delivery of the polynucleotide is preferably facilitated without need for injection by use of detergents, absorption promoters, chemical irritants (such as keratinolytic agents), or mechanical irritants. Detergents and absorption promoters which facilitate uptake of small molecules other than genes are well known in the art and may, without undue experimentation, be adapted for use in facilitating uptake of genes. Another substantially noninvasive approach to introducing the naked polynucleotides is by transdermal transmission (preferably iontophoresis) which has been used with success for transdermal transmission of peptides.

In general, use of any parenteral route of administration is possible, although use of routes involving little or no invasion of host tissues are greatly preferred. However, because of the need for repeated administration of the naked polynucleotide(s), intramuscular injections are not preferred. Instead, introduction of the naked polynucleotide(s) to an area of the body which is regenerative, such as skin and mucosa, is preferred for their ability to replace cells which have been directly affected by trauma associated with each dosage. Where desired, to ensure secretion of the proteins to be expressed in these embodiments of the invention, sequences controlling secretion known to those skilled in the art will be included in the administered naked polynucleotide, if not already present in the full-length gene. However, for use in immunizing a host to an antigen, it will be preferable for the antigen not to be secreted by APC's in which it is expressed, but rather presented on the cell surface. Thus, for use in embodiments of the invention which seek to immunize the host to an antigen, the naked polynucleotides will preferably be under the control of sequences which prevent secretion of expressed protein, which sequences are known to those of skill in the art.

Use of liposomes for delivery of the naked polynucleotides of the invention is not preferred. Rather, such use is likely to result in reduced levels of expression. This phenomenon is likely to be the result of impaired recognition by APC's of a liposome as an antigenic material.

BRIEF DESCRIPTION OF THE DRAWINGS

FIG. 11 depicts the levels of cytotoxic T cells detected in mice after injection of ovalbumin-encoding naked plasmids administered by intradermal injection.

DETAILED DESCRIPTION OF THE INVENTION

Figure 1A:
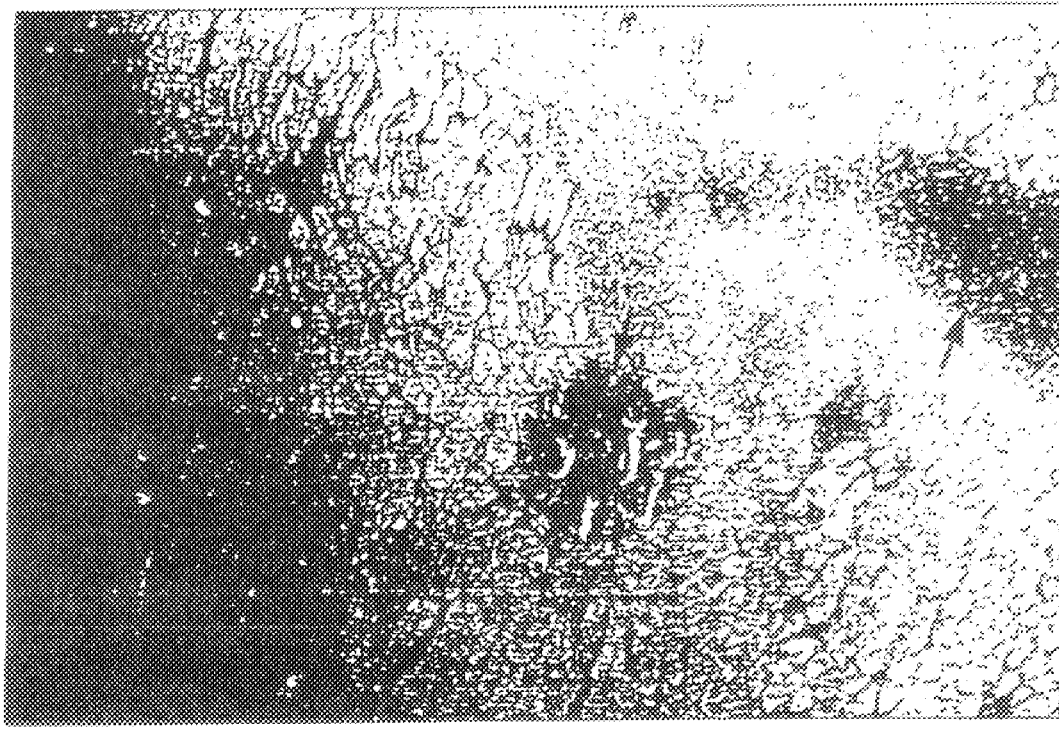
FIG. 1A depicts a section of muscle tissue demonstrating chronic inflammation and FIG. 1B depicts a section of muscle tissue displaying myonecrosis following intramuscular injections of pREVk3 and pRSVIL-2.
Figure 1B:
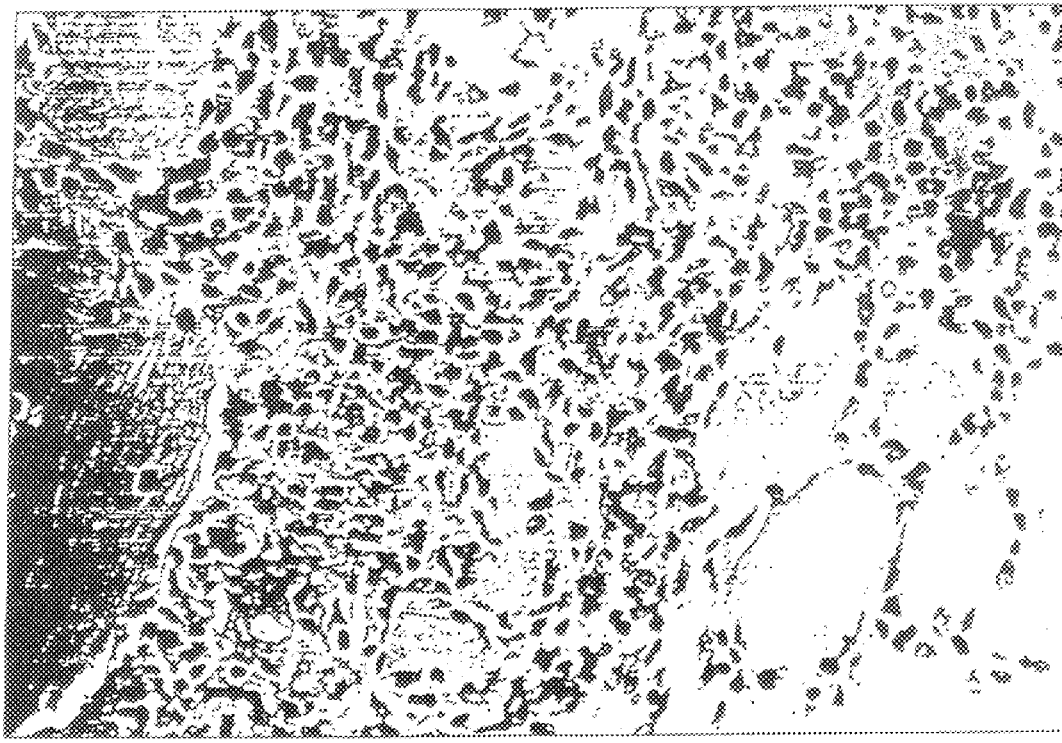

Throughout this description, the preferred embodiment and examples shown should be considered as exemplars, rather than limitations on the invention.

I. INTRODUCTION OF NAKED POLYNUCLEOTIDES INTO TARGET TISSUES HAVING SUBSTANTIAL CONCENTRATIONS OF ANTIGEN PRESENTING CELLS

A. Preparation of Naked Polynucleotides

The polynucleotides to be used in the invention may be DNA or RNA, but will preferably be a complementary DNA (CDNA) sequence. The polynucleotide sequences used in the invention must be (a) expressible and (b) either non-replicating or engineered by means well known in the art so as not to replicate into the host genome. Illustrations of the preparation of polynucleotides suitable for use in the invention follow and specific examples showing how particular polynucleotide compositions were made are provided infra. It will, however, be apparent to those skilled in the art that other known means of preparing nonreplicating polynucleotides may also be suitable.

Polynucleotides for use in the invention can be obtained using hybridization methods well known in the art. DNA and RNA may also be synthesized using automated nucleic acid synthesis equipment well known in the art. Use of the well-known polymerase chain reaction (PCR) is particularly preferred for generating mixtures of polynucleotides. Genomic nucleic acids may be prepared by means well-known in the art such as the protocols described in Ausubel, et al., *Current Protocols in Molecular Biology*, Chs. 2 and 4 (Wiley Interscience, 1989). cDNA can be synthesized according to means well known in the art (see, e.g., Maniatis, et al., *Molecular Cloning*; A Laboratory Manual (Cold Spring Harbor Lab, New York, 1982). A cDNA expression library containing polynucleotides of interest can also be screened by means well known in the art. For reference, examples of such means are illustrated by the discussion below.

Preferred polynucleotides for use in specific applications are suggested in the preceding Summary of the Invention. For example, the naked polynucleotides may operatively encode for therapeutic peptides, but will preferably encode for immunogenic peptides which can act as antigens to provoke a humoral and/or cellular response. The naked polynucleotides can also operatively encode for an antibody. In this regard, the term "antibody" encompasses whole immunoglobulin of any class, chimeric antibodies, hybrid antibodies with dual or multiple antigen specificities and fragments including hybrid fragments. Also included within the meaning of "antibody" are conjugates of such fragments, and so-called antigen binding proteins (single chain antibodies) as described, for example, in U.S. Pat. No. 4,704,692. Alternatively, the encoded antibodies can be anti-idiotypic antibodies (antibodies that bind other antibodies) as described, for example, in U.S. Pat. No. 4,699,880.

Those of skill in the art will, however, appreciated that the methods of the invention may be adapted for use in administering any polynucleotide or mixture thereof which operatively encode therapeutic and/or immunogenic peptides of interest. The invention is therefore not limited to use with any particular polynucleotide(s).

As used herein, "polynucleotide" refers to a polymer of deoxyribonucleotides or ribonucleotides, in the form of a separate fragment or as a component of a larger construct. DNA encoding an therapeutic and/or immunogenic peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code, which sequences may be readily determined by those of ordinary skill in the art.

Polynucleotide sequences encoding a desired therapeutic and/or immunogenic peptide can be expressed in either eukaryotes or prokaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are also well known in the art. Such vectors are used to incorporate DNA of the invention.

DNA sequences for use in producing therapeutic and/or immunogenic peptides of the invention can also be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). The development of specific DNA sequences encoding or fragments thereof, can also be obtained by: 1) isolation of double-stranded DNA sequences from the genomic DNA: 2) chemical manufacture of a DNA sequence to provide the necessary codons for the polypeptide of interest;and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture.

A cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucelotide of interest. Alternatively, a cDNA library can be screened indirectly for expression of therapeutic and/or immunogenic peptides having at least one epitope using antibodies specific for the peptides. Such antibodies can be either polyclonally or monoclonally derived and used to detect expression product indicative of the presence of cDNA of interest.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

The naked polynucleotides may be conjugated to or used in association with other polynucleotides which operatively code for regulatory proteins that control the expression of these polypeptides or may contain recognition, promoter and secretion sequences. Those of ordinary skill in the art will be able to select regulatory polynucleotides and incorporate them into the naked polynucleotides of the invention (if not already present therein) without undue experimentation. For example, suitable promoters for use in murine or human systems and their use are described in *Current Protocols in Molecular Biology*, supra at Ch. 1.

A particularly preferred form of a naked polynucleotide for use in the invention will be one which has been incorporated into a plasmid vector. Use of a plasmid vector, particularly one which comprises a replicator, will prolong expression of the gene in target tissues. Certain plasmid vectors are also good mediators of immune responses to immunogenic peptides because high levels of expression are achieved when the gene encoding the peptides is incorporated into the vector.

Suitable plasmid vectors are well-known in the art and include the vectors described in *Current Protocols in Molecular Biology*, supra at Ch. 1. Two particularly preferred plasmid vectors are the pRSV (Rous sarcoma virus) and pCMV (cytomegalovirus) promoter vectors. Of these promoters, CMV is preferred for polynucleotides to be introduced into tissue other than muscle. This preference is based on observations that higher levels of expression are achieved in this context when the CMV promoter is employed.

A suitable protocol for isolation of the RSV promotor and its use in construction of a plasmid vector is described in Gorman, et al., *Proc. Natl. Acad. Sci, USA,* 79:6777, (1982). Other preferred plasmid vectors are pREP7 and pREV which are commercially available from Invitrogen of San Diego, Calif. For cloning of polynucleotides, a particularly suitable plasmid for production of mRNA is the pSP64T cloning vector described by Kreig, et al., *Nucleic Acids Res.,* 12:7057–7070, (1984). Any cDNA containing an initiation codon can be introduced into this plasmid and mRNA prepared from the expressed DNA templates using conventional techniques.

Various viral vectors that can be utilized (albeit are not preferred for use) in the invention include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

For purposes of monitoring expression, these vectors may be modified to include known reporter genes. For example, the pRSV lac-Z DNA vector described in Norton, et al., *Mol. Cell. Biol.,* 5:281, (1985), may produce β-galactosidase with protein expression. Luciferase and chloramphenicol acetyl transferase ("CAT"; see, e.g., Gorman, et al., supra, re construction of a pRSV-CAT plasmid) may also be used. Convenient plasmid propagation may be obtained in *E. coli* (see, e.g., *Molecular Cloning: A Laboratory Manual*, supra.)

For use as a tolerizing vaccine, a mixture of polynucleotides or separately coadministered group of polynucleotides may include a gene operatively encoding for an immunosuppressive cytokine (such as TGFβ) and a separate gene operatively encoding for a relevant histocompatibility protein. This approach could be adapted for use in inducing tolerance to foreign antigens (including alloantigens) as well as self-antigens.

B. Pharmaceutical Preparations of Naked Polynucleotides

Compositions of naked polynucleotides and mixtures of polynucleotides may be placed into a pharmaceutically acceptable suspension, solution or emulsion. Suitable mediums include saline and may, for those embodiments which do not rely on antigen presenting cells for delivery of the polynucleotides into target tissue, liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of naked polynucleotides may be lyophilized using means well known in the art, for subsequent reconstitution and use according to the invention.

For those embodiments of the invention which do not rely on APC recognition of naked polynucleotides as antigen, in addition to the targeted vector delivery systems discussed supra, a colloidal dispersion system may also be used for targeted delivery. However, it will be appreciated by those of skill in the art that the advantages of employing the method of the invention to administer naked nucleotides, and of administering those nucleotides to tissues having relatively high concentrations of antigen presenting cells, are such that the use of collodidal dispersion systems for delivery of polynucleotides will not be a preferred method. The discussion below regarding such systems is therefore provided principally for reference in the event that the preferred method of the invention is determined to be unavailable for use with respect to a particular indication.

Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules.

RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

For those embodiments of the invention which do rely on APC expression, liposomal preparations substantially limit uptake of the naked polynucleotides in vivo and should not be used. Instead, isotonic buffered solution is the preferred medium for maximal uptake of the naked polynucleotides in such embodiments. Further, use of absorption promoters, detergents, chemical irritants or mechanical irritation means is also preferred to enhance transmission of the naked polynucleotide composition through the point of entry. For reference concerning general principles regarding promoters and detergents which have been used with success in mucosal delivery of organic and peptide-based drugs, see Chien, *Novel Drug Delivery Systems*, Ch. 4 (Marcel Dekker, 1992). Specific information concerning known means and principles of nasal drug delivery are discussed in Chien, supra at Ch 5. Examples of suitable nasal absorption promoters are set forth at Ch. 5, Tables 2 and 3; milder agents are preferred. Further, known means and principles of transdermal drug delivery are also discussed in Chien, supra, at Ch. 7. Suitable agents for use in the method of this invention for mucosal/nasal delivery are also described in Chang, et al., *Nasal Drug Delivery*, "Treatise on Controlled Drug Delivery", Ch. 9 and Table 3-4B thereof, (Marcel Dekker, 1992). Suitable agents which are known to enhance absorption of drugs through skin are described in Sloan, *Use of Solubility Parameters from Regular Solution Theory to Describe Partitioning-Driven Processes*, Ch. 5, "Prodrugs: Topical and Ocular Drug Delivery" (Marcel Dekker, 1992), and at places elsewhere in the text.

It is expected that these techniques (and others which are conventionally used to facilitate drug delivery) may be adapted to preparation of naked polynucleotides for use in the methods of the invention by those of ordinary skill in the art without undue experimentation. In particular, although the approaches discussed in the preceding paragraphs have not, to the inventors' knowledge, been previously used for polynucleotide delivery, it is believed that they are suitable for use to that end. For that reason, the references identified above, while not essential to the inventive methods, are incorporated herein by this reference. Specific examples illustrating this suitability are set forth infra.

C. Means For, And Routes Of, Administration of Naked Polynucleotides

For dermal routes of administration, the means of introduction may be by epidermal administration, subcutaneous or intradermal injection. Of these means, epidermal administration is preferred for the greater concentrations of APC's expected to be in intradermal tissue.

The means of introduction for dermal routes of administration which are most preferred, however, are those which are least invasive. Preferred among these means are transdermal transmission and epidermal administration.

For transdermal transmission, iontophoresis is a suitable method. Iontophoretic transmission may be accomplished using commercially available "patches" which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH product; those instructions are incorporated herein by this reference.

Epidermal administration essentially involves mechanically or chemically irritating the outermost layer of the epidermis sufficiently to provoke an immune response to the irritant. Specifically, the irritation should be sufficient to attract APC's to the site of irritation. As discussed previously, it is believed that the APC's then take up and express the administered naked polynucleotide.

An exemplary mechanical irritant means employs a multiplicity of very narrow diameter, short tynes which can be used to irritate the skin and attract APC's to the site of irritation, to take up naked polynucleotides transferred from the end of the tynes. For example, the MONO-VACC old tuberculin test manufactured by Pastuer Merieux of Lyon, France contains a device suitable for introduction of naked polynucleotides.

The device (which is distributed in the U.S. by Connaught Laboratories, Inc. of Swiftwater, Pa.) consists of a plastic container having a syringe plunger at one end and a tyne disk at the other. The tyne disk supports a multiplicity of narrow diameter tynes of a length which will just scratch the outermost layer of epidermal cells. Each of the tynes in the MONO-VACC kit is coated with old tuberculin; in the present invention, each needle is coated with a pharmaceutical composition of naked polynucleotide or a mixture thereof. Use of the device is according to the manufacturer's written instructions included with the device product; these instructions regarding use and administration are incorporated herein by this reference to illustrate conventional use of the device. Similar devices which may also be used in this embodiment are those which are currently used to perform allergy tests.

Another suitable approach to epidermal administration of naked polynucleotides is by use of a chemical which irritates the outermost cells of the epidermis, thus provoking a sufficient immune response to attract APC's to the area. An example is a keratinolytic agent, such as the salicylic acid used in the commercially available topical depilatory creme sold by Noxema Corporation under the trademark NAIR. This approach may also be used to achieve epithelial administration in the mucosa. The chemical irritant may also be applied in conjunction with the mechanical irritant (as, for example, would occur if the MONO-VACC type tyne were also coated with the chemical irritant). The naked polynucleotide may be suspended in a carrier which also contains the chemical irritant or coadministered therewith.

For mucosal administration, the means of introduction will vary according to the location of the point of entry. Particularly for immunization to and treatment of respiratory infections, intranasal administration means are most preferred. These means include inhalation of aerosol suspensions or insufflation of the naked polynucleotide or mixtures thereof. Suppositories and topical preparations will also be suitable for introduction to certain mucosa, such as genital and ocular sites. Also of particular interest with respect to vaginal delivery of naked polynucleotides are vaginal sandwich-type rings and pessaries. Examples of these devices and their use are described in Chien, supra at Ch. 9.

The dosage of each naked polynucleotide or mixture thereof to be supplied using the method of the invention will vary depending on the desired response by the host and the polynucleotide used. Generally, it is expected that up to 100–200 $\mu$g of DNA can be administered in a single dosage, although as little as about 0.3 $\mu$g of DNA administered through skin or mucosa can induce long lasting immune responses.

For purposes of the invention, however, it is sufficient that the naked polynucleotides be supplied at a dosage sufficient to cause expression of the biologically active peptide encoded by the polynucleotide. Dosages suitable for particular indications are illustrated by the discussion and examples provided below.

These dosages may be modified to achieve therapeutic, subtherapeutic or immunogenic levels of expression. Means to confirm the presence and quantity of expressed peptides are well-known to those skilled in the art and will not, therefore, be described in detail. Certain such means are illustrated in the Examples provided below; generally, they include immunoassays (such as enzyme-linked immunosorbent assays), PCR techniques, and immunohistological analyses performed according to techniques which are well known in the art. Dosages of the administered polynucleotides can be adjusted to achieve the desired level of expression based on information provided by these detection and quantification means as well as in vivo clinical signs known to practitioners skilled in the clinical arts.

II. ADMINISTRATION OF NAKED POLYNUCLEOTIDE COCKTAILS

Another aspect of the invention is the administration of a peptide cocktail (i.e., mixture of polynucleotides) via expression of gene constructs containing, for example, up to 200 polynucleotide sequences under the control of a single promoter. This embodiment will be of particular use in treating infections by agents of different species which cause similar symptoms. For example, there are over 100 known species of rhinoviruses which cause respiratory illnesses having similar clinical symptoms. Rather than undertaking the identification of the particular infecting species (a laborious and often inexact process), a cocktail vaccine could be administered according to the method of the invention which is capable of stimulating an immune response to many different rhinoviruses. This approach also allows for the construction of a vaccine to various strains of HIV, using pooled isolates of envelope genes from different patients (which genes may, if necessary, then be amplified).

Administration of mixtures of polynucleotides could also serve to deliver peptides having more than one biological activity. For example, a naked polynucleotide operatively encoding for an immunogenic peptide may be coupled to or administered with a naked polynucleotide operatively encoding an antibody in such a way that both peptide and antibody will be expressed. To illustrate, administration of genes which will jointly express IL-2 and anti-gp71 may (based on results obtained with the IL-2 protein) result in localization of the antibody in tumor tissue developed in response to murine leukemia virus (MuLV) in mice (see, re results obtained with concurrent administration of IL-2/anti-gp71 mAb's, Schultz, et al., *Cancer Res.* 50:5421–5425, 1990).

III. USE OF THE METHOD OF THE INVENTION TO TREAT ALLERGIES

An other aspect of the invention is the administration of naked polynucleotides which operatively encode for proteinaceous allergens or peptide fragments thereof to induce immunity to the allergen without inducing IgE antibody production. Specifically, the method is designed to selectively boost production of TH1 (helper T cell) lymphocytes in preference to the allergenic stimulation of TH2 lymphocyte mediated production of IgE antibody.

In mice, IgG 2A antibodies are serological markers for a TH1 type immune response, whereas IgG 1 antibodies are indicative of a TH2 type immune response. TH2 responses include the allergy-associated IgE antibody class; soluble protein antigens tend to stimulate relatively strong TH2 responses. In contrast, TH1 responses are induced by antigen binding to macrophages and dendritic cells. As shown in the data presented in Examples 12 and 13, mice injected intradermally with antigen-encoding polynucleotides preferentially produced IgG2A antibodies indicative of TH1 responses, which in turn are indicative of the antigen being expressed intracellularly in, then presented by, APCs. In contrast, mice injected intradermally with antigen preferentially produced IgG1 antibodies indicative of a predominant TH2 cell response.

This embodiment of the invention is based on the unexpected discovery that, in contrast to allergy immunotherapy with intact allergens, administration of naked polynucelotides which encode the allergens (or fragments thereof not only suppresses IgE antibody production, but also does so from the outset of therapy, thus avoiding the risk of anaphylaxis posed by conventional allergen immunotherapy. Specifically, administration of allergen-encoding naked polynucelotides (particularly through dermal and epidermal routes) selectively stimulates the production of CD4+ TH1 and CD8+ lymphocytes over CD4+ TH2 lymphocytes, as well as stimulating INFγ secretion (which suppresses IgE antibody activity).

Over the last few years it has been shown that CD4+ cells generally fall into one of two distinct subsets, the TH1 and TH2 cells. TH1 cells principally secrete IL-2, IFNγ and TNFβ (the latter two of which mediate macrophage activation and delayed type hypersensitivity) while TH2 cells principally secrete IL4 (which stimulates production of IgE antibodies), IL-5, IL-6 and IL-10. These CD4+ subsets exert a negative influence on one another; i.e., secretion of TH1 lymphokines inhibits secretion of TH2 lymphokines and vice versa. In addition, it is believed that exposure of TH2 cells to cytotoxic T lymphocytes ("CTL's") also suppresses TH2 cell activity.

How the helper T cell subsets are differentially regulated is not completely clear. Factors believed to favor TH1 activation resemble those induced by viral infection and include intracellular pathogens, exposure to IFNγ and IL-2, the presence of APCs and exposure to low doses of antigen. Factors believed to favor TH2 activation include exposure to IL-4 and IL-10, APC activity on the part of B lymphocytes and high doses of antigen. Active TH1 (IFNγ) cells enhance cellular immunity and are therefore of particular value in responding to intracellular infections, while active TH2 cells enhance antibody production and are therefore of value in responding to extracellular infections. However, in the allergy context, TH2 cell activity also induces IgE production through the release of IL-4, thus encouraging the formation of IgE-allergen complexes and stimulation of allergic responses.

As reflected in the data presented in Examples XI and XII, intradermal challenge with a protein allergen (β galactosidase) selectively induces TH2 responses in mice which, consistent with the theory of allergen immunotherapy, is gradually replaced by a TH1 response in allergen desensitized mice. However, as demonstrated in Example XIII, IgE antibody levels produced in the protein injected mice were substantially greater during the initial phase of treatment than were produced at any stage of treatment of mice injected with a polynucleotide that operatively encoded the same allergen.

Further, in the mice challenged with an intradermal dose of an allergen-encoding plasmid (pCMV-Lac Z; see, Examples XI and XII), the TH1 cell responses greatly exceeded those of TH2 cells. Even more surprisingly, IgE and IL-4 levels in the pCMV-Lac Z challenged mice were very low (Examples XIII and XIV), while allergen-specific CTL levels (Example XV) and TH1 cell secretion of INFγ (Example XIV) were enhanced as compared to protein challenged and control mice. Moreover, the protection against IgE production afforded to the pCMV-Lac Z challenged mice continued despite subsequent challenge with the plasmid or protein, even when combined with adjuvant (Example XII). Thus, as opposed to conventional allergen immunotherapy, the allergen-encoding gene immunotherapy of the invention abrogates both allergen specific and non-specific IgE production and protects the host from further production of IgE even on subsequent allergen challenge.

The explanation of why introduction of an allergen via expression as a gene product induces desensitization to the allergen without inducing the same magnitude of antibody response induced on introduction of the allergen itself is not entirely clear. However, without limiting the invention to a particular mechanism of action, it is probable that introduction of low doses of allergen-encoding polynucleotide to APC's using the method of the invention causes the allergen to be expressed and retained intracellularly, thus limiting the extracellular availability of the allergen for stimulation of IgE antibody production and formation of allergen/IgE antibody complexes. Conversely, it appears that introduction of relatively "high" doses of allergen-encoding polynucleotides (e.g., substantially greater than about 50 μg in mice) can stimulate production of IgE antibody at levels that are more comparable to those produced in mice injected subcutaneously with an allergen, possibly due to extracellular release of excessive antigen.

Thus, the preferred embodiment of the method for treatment of allergies of the invention will be one in which the allergen-encoding polynucleotide is administered in "low" doses (e.g., preferably less than about 50 μg in mice). Those of ordinary skill in the art will readily be able to determine an equivalent dosage level for use in humans. Those of ordinary skill in the art will be familiar with the course of dosing employed in allergen immunotherapy (i.e., priming, booster and maintenance dosing), which course will be suitable for use in the method of the invention. Generally, it can be expected that doses of less than about 50 μg, and even less than about 10 μg, will be suitable for priming, booster and maintenance doses in humans. Alternatively, the priming dose of allergen-encoding polynucleotide may be followed by booster and/or maintenance doses of allergen. As shown in Examples VII, X, XII and XV, once tolerance to the allergen has been induced through introduction of an allergen-encoding polynucleotide, that tolerance is maintained despite subsequent allergen challenge.

It is generally accepted in the art that allergen tolerance through allergen immunotherapy has only been achieved at therapeutically significant levels (e.g., wherein the patient's allergy symptoms are noticeably reduced) when the allergen is introduced intradermally (typically, by subcutaneous injection). Efforts to induce tolerance to an allergen using oral, sublingual, inhalation and local nasal routes of administration have not been very successful in suppressing IgE antibody response to allergen challenge. Thus, means for intradermal introduction of allergens for use in allergen immunotherapy have been developed whose use is familiar to physicians experienced in the treatment of allergies, such as the MONOVACC® tyne device described elsewhere above.

As also described elsewhere above, the naked polynucleotides of the invention may be effectively administered by mechanical irritation of the epidermis and dermis using devices such as the MONOVACC® tyne device. Because dermal and epidermal routes for administration of naked polynucleotides enhances their introduction into APC's, and because intradermal administration of allergens is believed to be the most efficacious route for use in allergen immunotherapy, the most preferred routes of administration for allergen-encoding polynucleotides to treat allergies will be penetration or mechanical irritation of the dermis and epidermis.

A particularly efficacious method for introduction of allergen-encoding polynucleotides to treat allergy is mechanical or chemical irritation of the dermis and epidermis. One particularly convenient means of administering such polynucleotides is by the use of a multiple tyne device whose tines have been coated with more than one allergen-encoding polynucleotide. An example of a tyne device suitable for this use is the MULTITEST® multiple skin test applicator manufactured by Lincoln Diagnostics of Decatur, Ill. For use in conventional allergen immunotherapy, the tyne device is typically placed onto a multiple chambered platform whose chambers each contain allergen extracts so the tips of each tyne are immersed in extract. After immersion, the device is placed onto the patient's skin, preferably at a site where sufficient tissue is present to permit simultaneous subcutaneous penetration by all of the tines. The patient's reaction to each allergen is evaluated visually based on the formation and relative size of wheals on the skin at the site of entry for each tyne. Most preferably, the appearance of each injection site is compared to positive and negative control injections (with, for example, histamine and glycerin).

The same approach may be used for the allergen-encoding polynucleotide immunotherapeutic method of the invention. As demonstrated in Examples V, XII and XIII, the tynes of a tyne device such as the MULTITEST® device may be coated with allergen-encoding polynucleotides by immersing the tips of the tines into an aqueous solution of the polynucleotides. For convenience, the tyne device may then be frozen so that the polynucleotides become dried onto the tines and can be administered without having to prepare the device for use at the time of treatment.

The polynucleotides may encode more than one allergen, different peptides of an allergen, or a combination of the two. The polynucleotides may encode for intact allergen, T cell epitope(s) of an allergen, and/or either engineered by means well-known in the art to be non-secreting. Many allergen-encoding polynucleotides are known in the art; others can be identified using conventional techniques such as those described elsewhere above (see, Section I(A)). Examples of known allergen-encoding polynucleotides include cDNAs which code for IgE reactive major dust mite allergens Der pI and Der pII (see, Chua, et al., *J. Exp. Med.*, 167:175–182, 1988; and, Chua, et al., *Int. Arch. Allergy Appl. Immunol.*, 91:124–129, 1990), T cell epitope peptides of the Der pII allergen (see, Joost van Neerven, et al., *J. Immunol.*, 151:2326–2335, 1993), the highly abundant Antigen E (Amb al) ragweed pollen allergen (see, Rafner, et al., *J. Biol. Chem.*, 266:1229–1236, 1991), phospholipase $A_2$ (bee venom) allergen and T cell epitopes therein (see, Dhillon, et al., *J. Allergy Clin. Immunol.*, 90:42–51, 1992), white birch pollen (BetvI) (see, Breiteneder, et al., EMBO, 8:1935–1938, 1989), and the Fel dI major domestic cat allergen (see, Rogers, et al., *Mol. Immunol.*, 30:559–568, 1993). The published sequences and methods for their isolation and synthesis described in these articles are incorporated herein by this reference to illustrate knowledge in the art regarding allergen-encoding polynucleotides.

To minimize, if not avoid, extracellular stimulation of IgE antibody formation against expressed allergen, the allergen-encoding polynucleotides administered according to the invention will preferably be administered as part of a non-secreting recombinant expression vector. Another particularly useful vector for administration of any naked polynucleotides according to the invention are those which contain a promoter that can be switched "on" or "off" after the vector has been administered to the patient.

Particularly efficacious examples of such promoters are the ligand inducible nuclear receptor promoters. Nuclear receptors represent a family of transcriptional enhancer factors that act by binding to specific DNA sequences found in target promoters known as response elements. Specific members of the nuclear receptor family include the primary intracellular targets for small lipid-soluble ligands, such as vitamin $D_3$ and retinoids, as well as steroid and thyroid hormones ("activating ligands").

Figure 21:
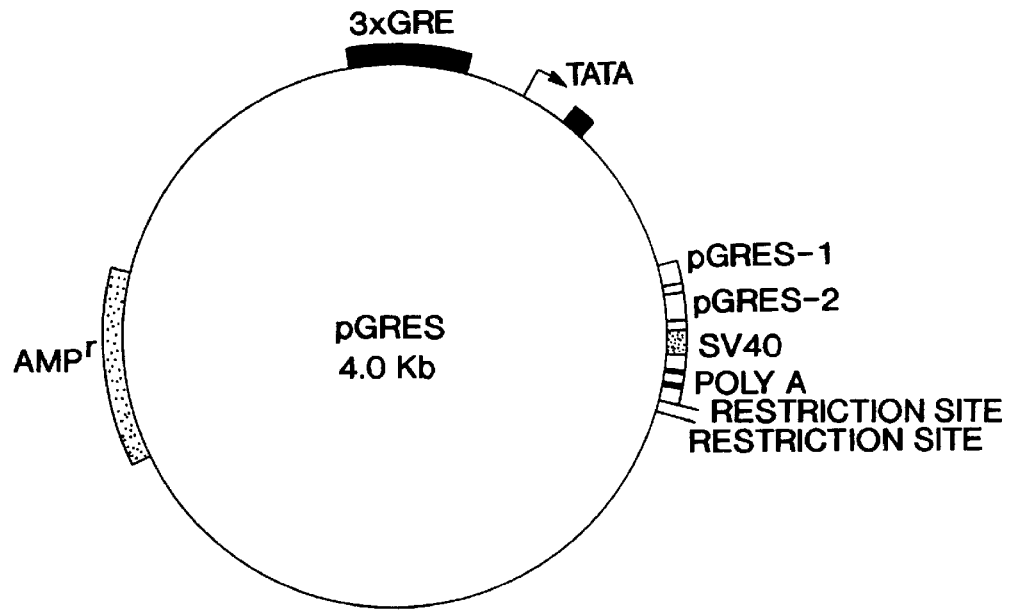
FIG. 21 is a map of the pGREtk eukaryotic expression vector.

Nuclear receptors activated by specific activating ligands are well suited for use as promoters in eukaryotic expression vectors since expression of genes can be regulated simply by controlling the concentration of ligand available to the receptor. For example, glucocorticoid-inducible promoters such as that of the long terminal repeat of the mouse mammary tumor virus (MMTV) have been widely used in this regard because the glucocorticoid response elements are expressed in a wide variety of cell types. One expression system which exploits glucocorticoid response elements responsive to a wide variety of steroid hormones (e.g., dexamethasone and progesterone) is a pGREtk plasmid (containing one or more rat tyrosine amino transferase glucocorticoid response elements upstream of the herpes simplex virus thymidine kinase (tk) promoter in pBLCAT8+), transfected in HeLa cells (see, Mader and White, *Proc. Natl. Acad. Sci USA*, 90:5603–5607, 1993 [pGRE2tk]; and, Klein-Hitpass, et al., *Cell*, 46:1053–1061, 1986 [pBLCAT8+]; the disclosures of which are incorporated herein by this reference to illustrate knowledge in the art concerning construction of suitable promoters derived from nuclear receptor response elements ["NRRE promoters"]). The pGREtk promoter (see, map at FIG. 21) is particularly effective in stimulating controlled overexpression of cloned genes in eukaryotic cells (Mader and White, supra at 5607).

Another particularly suitable NRRE promoter for use in the invention is one which is inducible by the vitamin $D_3$ compound 1,25-dihydroxyvitamin $D_3$ and non-hypercalcemic analogs thereof (collectively, "vitamin $D_3$ activating ligands"). NRRE promoters inducible by vitamin $D_3$ activating ligands contain the vitamin $D_3$ receptor (VDR) response elements PurG(G/T)TCA which recognizes direct repeats separated by 3 base pairs. Vitamin $D_3$ response elements are found upstream of human osteocalcin and mouse osteopontin genes; transcription of these genes is activated on binding of the VDR (see, e.g., Morrison and Eisman, *J. Bone Miner. Res.*, 6:893–899, 1991; and, Ferrara, et al., *J. Biol. Chem.*, 269:2971–2981, 1994, the disclosures of which are incorporated herein by this reference to illustrate knowledge in the art of vitamin $D_3$ responsive inducible promoters). Recent experimental results from testing of a recombinant expression vector containing the mouse osteopontin VDR upstream of a truncated herpes simplex virus thymidine kinase (tk) promoter suggested that 9-cis-retinoic acid can augment the response of VDR to 1,25-hydroxyvitamin $D_3$ (see, Carlberg, et al., *Nature*, 361:657–660, 1993).

Figure 22:
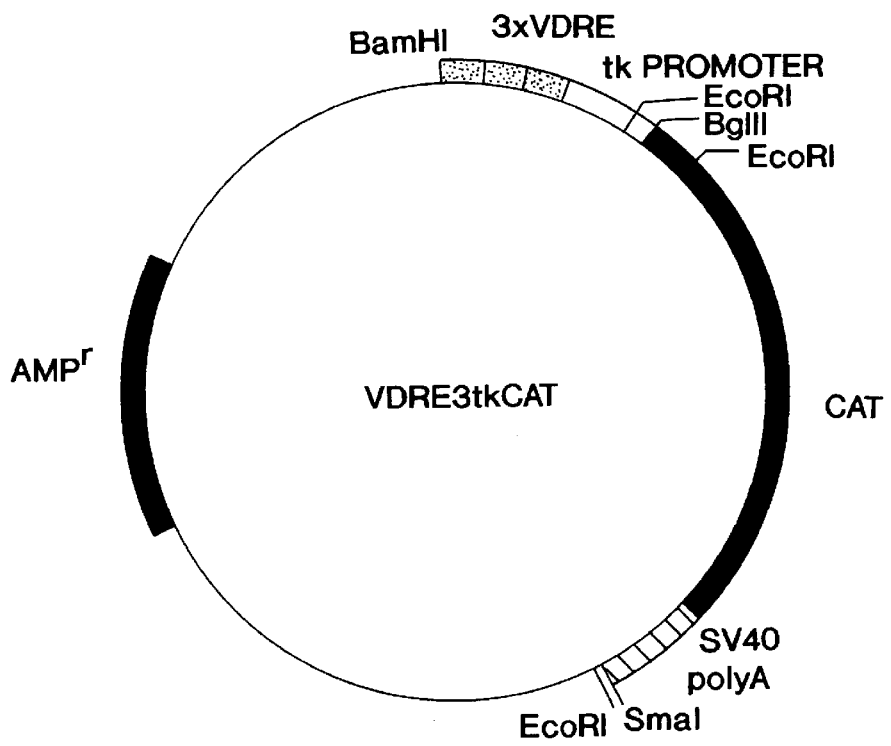
FIG. 22 is a map of the pVDRtk eukaryotic expression vector.

Ferrara, et al. also described vitamin $D_3$ inducible promoters in recombinant expression vectors constructed using multiple copies of a strong VDR; in particular, the mouse osteopontin VDR (composed of a direct repeat of PurGT-TCA motifs separated by 3 base pairs). This VDR conforms to the PurGG/TTCA consensus motifs which have previously been shown to be responsive not only to vitamin $D_3$, but also to thyroid hormone and/or retinoic acid. As many as three copies of the mouse VDR was inserted into pBLCAT8+; immediately upstream of the herpes simplex virus tk promoter (see, e.g., FIG. 22 [map of pVDREtk]). Transfection of the resulting VDREtk vector into COS cells (producing a "VDR expression system") proved to be particularly useful in that COS cells contain the nuclear retinoid X receptor (RXR) that has been shown to act as an auxiliary factor for binding of VDR to its response element.

The VDR expression system (and functionally equivalent expression systems under the control of, for example, human osteocalcin gene promoter) is uniquely suited for use in the invention. Specifically, expression of a naked polynucleotide administered to a mammal according to the invention by epidermal or dermal routes (particularly the former) in a vitamin $D_3$ responsive expression system can be switched on by topical administration of a 1,25-dihydroxyvitamin $D_3$ preparation at the point of entry (and off by withdrawing the vitamin $D_3$ preparation and/or modulated by applying or withdrawing a source of retinoic acid to or from the point of entry). Conveniently, 1,25-dihydroxyvitamin $D_3$ and non-hypercalcemic analogs thereof have been approved for use in topical preparations by the United States Food and Drug Administration for the treatment of psoriasis and are commercially available.

In vivo tests of the NRRE promoters in human skin indicate that they are inducible on systemic exposure to their corresponding response elements (see, Tsou, et al., *Exp. Cell Res.*, 214:27–34, 1994 [retinoic acid activation of retinoic acid response element coupled to a Lac-Z reporter molecule in epidermis of transgenic mice]). Given the expected retention of polynucleotides administered dermally or epidermally at the point of entry (thus making them available for exposure to topically absorbed response elements; see, e.g., discussion at pages 15–16 and data in Example IV), it can be reasonably predicted that use of NRRE promoters for expression of such polynucleotides will also permit their in vivo control through topical administration of appropriate NRRE promoter activating ligands (e.g., 1,25-dihydroxyvitamin $D_3$ transcriptional activators with a VDR expression vector for expression of the polynucleotide of interest).

Thus, use of an NRRE promoter recombinant expression vector for administration and expression of naked polynucleotides according to the invention permits control of expression to, for example, switch on expression when dosing is needed or switch off expression in the event of an adverse reaction to the expressed protein or peptide.

Examples illustrating aspects of each embodiment of the invention are provided below. They should be regarded as illustrating rather than limiting the invention.

EXAMPLE I

LOCALISED DELAYED HYPERSENSITIVITY RESPONSES IN MICE OCCUR FOLLOWING INTRAMUSCULAR INJECTIONS OF NAKED POLYNUCELOTIDE

Although (consistent with previously reported results) intramuscular injection of naked plasmid cDNA results in expression of peptides encoded by the polynucleotides, it also (contrary to previously reported results) elicits an immune response to the gene in the muscle tissue. With co-injection of 2 plasmids, this inflammatory response becomes chronic, with myonecrosis being exhibited. Both responses are consistent with a diagnosis of a localized delayed hypersensitivity response to the gene at its point of entry, i.e., muscle tissue. Contrary to previous assumptions, it is this inflammatory response rather than uptake by muscle cells which is likely (if not solely) responsible for expression of naked polynucleotides following intramuscular injections thereof. To illustrate the immune response caused by intramuscular injection of naked cDNA, pREVk3 and pRSVIL2 were prepared as follows.

Preparation of Plasmids

A rearranged kappa light gene from a human patient with chronic lymphocytic leukemia was isolated which contains a Humkv 325 (which encodes the 17.109 cross-reactive idiotype commonly expressed by IgM autoantibodies and chronic lymphocytic leukemia cells). This gene is known in the art and is described, for example, in Martin, et al *J. Exp. Med.*, 175:983, (1992), which article is incorporated herein by this reference.

A 1040 bp HindIII-XhoI fragment containing the V-J region of this gene was excised and inserted into the polycloning site of the mammalian expression vector pREP7 (Invitrogen, San Diego, Calif.), downstream of the Rous sarcoma virus (RSV) long terminal repeat (LTR) to produce a vector designated pREVk3. Downstream of the rearranged JK1 segment, there is a natural stop codon, which terminates translation.

To produce an IL-2 expression vector, designated pRSVIL-2, the luciferase cDNA in the vector pRSVL (Wolff, et al., *Science*, 247:1465, 1990) was replaced with a 680 bp HindIII-BamHI fragment of pBC12/HIV/IL-2 (American Type Culture Collection, No. 67618) according to the method taught in Cullen, *Cell*, 46:937, (1986). The Wolff, et al., and Cullen references are incorporated herein to illustrate knowledge in the art concerning construction of these expression vectors.

Intramuscular injection of mice with plasmid cDNA

Eight week old BALB/c mice were anesthetized with methoxyflurane. Plasmid cDNA (100 µg per injection) was suspended in 100 µl of saline, and then was injected four times into the quadricep muscles through a 28-gauge needle at weekly intervals. One group of six mice received 100 µg of pREVk3. Another group of six mice received 100 µg each of pREVk3 and pRSVIL-2 while a third group received 100 µg of saline alone. Just before every injection, blood samples were collected from the orbital arteries.

ELISA To Verify In Vivo Gene Expression by the Plasmids

Antibodies against Humkv325 products were measured by ELISA (enzyme-linked immunosorbent assay). The IgM rheumatoid factor Glo is encoded by the Humkv325 gene and has 17.109 idiotype positive kappa light chains. The purified protein was dissolved at 10 µg/ml in 0.1M borate, 0.2M NaCl, pH8.2 (i.e., buffered borate saline or BBS), and then 100 µl aliquots were added to the wells of plastic microtiter plates. After overnight incubation at 4° C., the plates were washed twice with BBS containing 0.5% Tween-20 (BBS/Tween), and were quenched with BBS supplemented with 1% bovine serum albumin (BBS/BSA) for four hours at room temperature. After washing twice with BBS/Tween, samples diluted serially in BBS/BSA were distributed to the wells in duplicate. After incubation for three hours at room temperature, the plates were washed four times with BBS/Tween, and then were incubated with biotinylated gout antimouse IgG (Kirkegaard & Perry, Gaithersburg, Md.) diluted to 1:2000 in BBS/BSA. One hour later, the plates were washed four times with BBS/Tween, and incubated with 25 µl of TMB peroxidase substrate (Kirkegaard & Perry). Thirty minutes later absorption at 450 nm was measured in a microplate reader (Molecular Devices, Menlo Park, Calif.). To estimate the antibody content in the immune sera, the results were compared to a standard curve made with monoclonal antibody 17.109 (see, e.g., the description of this mAb at Carson, et al., (1983) *Mol. Immunol.* 20:1081–1087).

These assays showed that production of the antibodies of interest had been enhanced, thereby confirming expression of the genes by the plasmids.

Histological evaluation

At day 49 the intramuscularly injected mice were sacrificed. Muscles into which the genes had been injected were fixed in 10% formalin and processed for histological evaluation.

Figure 1C:
FIG. 1C depicts sections of similar muscle tissue following subcutaneous injections of pREVK3 or pRSVIL-2.

Sections from muscles that had been co-injected with pREVk3 and pRSVIL2, demonstrated chronic inflammation and myonecrosis, consistent with a localized delayed hypersensitivity response (FIGS. 1A and B). In contrast, muscles injected with pREVk3 or pRSVIL2 alone had a lymphoid infiltrate localized to the site of subcutaneous injection (FIG. 1C).

EXAMPLE II

GENE EXPRESSION FOLLOWING INTRADERMAL INJECTION OF A NAKED POLYNUCLEOTIDE

To explore alternatives to intramuscular injections of naked polynucleotides, mice were injected with a naked cDNA plasmid intradermally. Gene expression was observed and measured.

The gene for influenza ribonucleoprotein (RNP) was subcloned into a pCMV plasmid as described above. RNP genes from numerous strains of influenza are known in the art and are highly conserved in sequence among various strains (see, e.g. Gorman, et al., *J. Virol,* 65:3704, 1991).

Four eight week old Balb/c mice were injected three times with 15 µg of pCMV-RNP suspended in 100 µl of HBSS. Injections were made intradermally at the base of the tails at two week intervals. Cytotoxic T lymphocytes (CTL) recognize antigens presented by class I MHC molecules and play an important role in the elimination of virally infected cells. Intramuscular (i.m.) immunization by means of cDNA expression vectors should be an effective method to introduce antigen into class I MHC molecules and thus stimulate CTL responses. In this study, intradermal (i.d.) injection of a plasmid containing the influenza nucleoprotein (NP) antigen gene induced both NP-specific CTL and high titers of anti-NP antibodies. These antibodies reached a maximum 6 weeks after injection and persisted unchanged for at least 28 weeks, in the absence of local inflammation.

Plasmid DNA was purified by CsCl banding in the presence of ethidium bromide and was stored frozen in 10 mM Tris-HCL, 0.1 mM EDTA, pH 8.0. Before injection, the plasmid was precipitated in ethanol and dissolved in normal saline containing 0.1 mM EDTA.

Figure 2A:
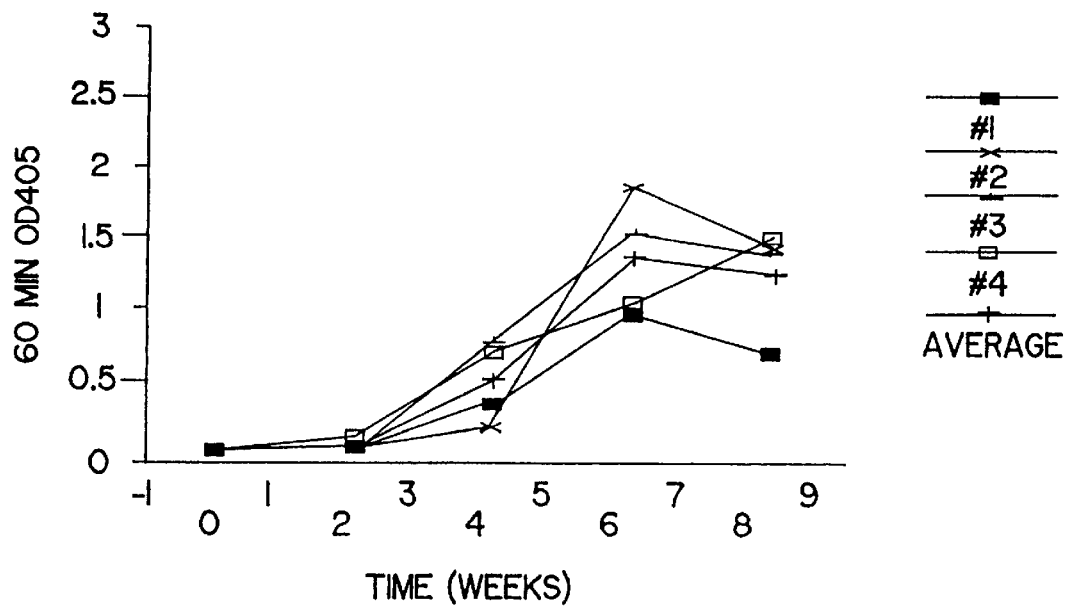
FIG. 2A depicts the results of an ELISA for anti-NP IgG in serum following intradermal injection of naked PCMVRNP.
Figure 2B:
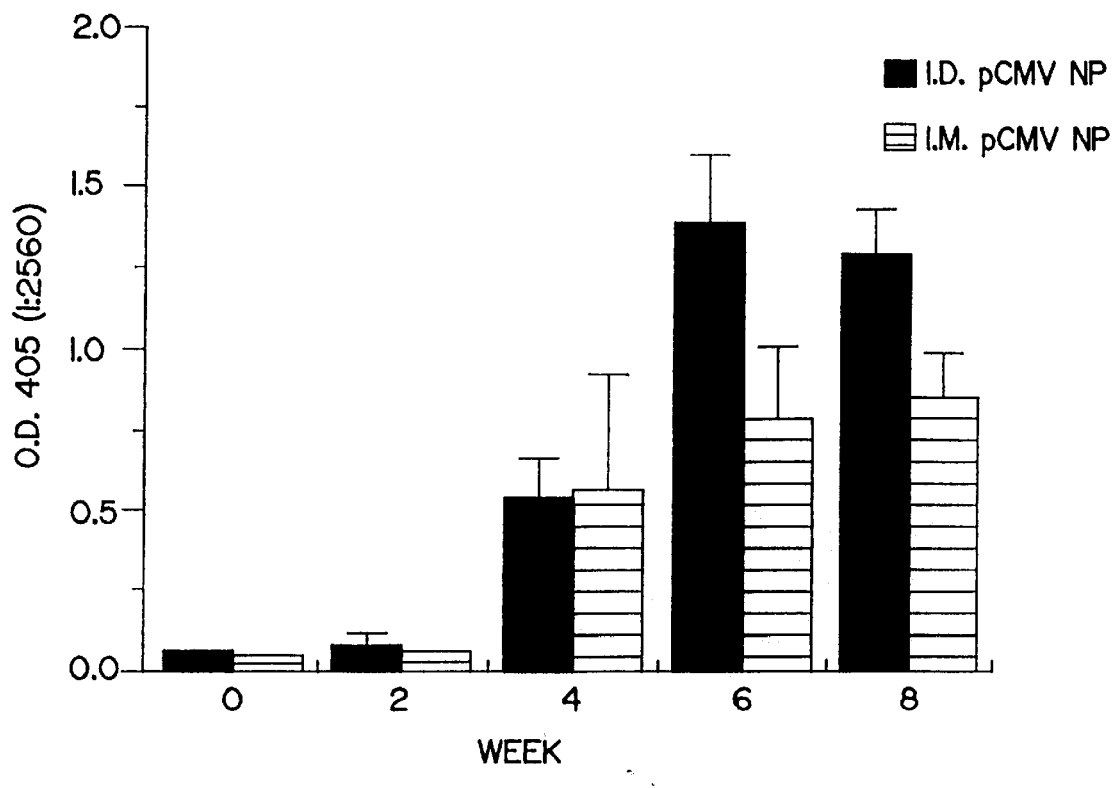
FIG. 2B depicts the results of an ELISA for anti-NP IgG in serum following intramuscular injection of naked pCMVRNP.

The presence of anti-NP IgG in serum was measured by ELISA substantially as described in Viera, et al., *Int. Immunl.,* 2:487, (1990). The results of this assay are shown in FIG. 2A; all of the animals developed high titer anti-NP antibodies, which persisted for more than 20 weeks. As shown in FIG. 2B, the intradermal injections appeared to give about four fold higher antibody titers than intramuscular injections (made as described in Example I) of equivalent amounts of plasmid DNA.

The axes of FIG. 2 represent, respectively, the ELISA titer (mean, 1 ounce) against time. Serum dilution for all graph points is 2560.

EXAMPLE III

GENE EXPRESSION FOLLOWING INTRANASAL INTRODUCTION OF A NAKED POLYNUCLEOTIDE

Using the same plasmid (pCMV-RNP) in the same HBSS suspension described in Example II, naked polynucleotide encoding for influenza ribonucleoprotein was introduced to Balb/c mice in 3 groups of 6 intranasally. Levels of anti-NP IgG in peripheral blood before and after introduction of the plasmid at various serum dilutions were measured by ELISA as described in Example II. Blood was drawn from each mouse after intranasal introduction after 6 weeks.

Figure 3:
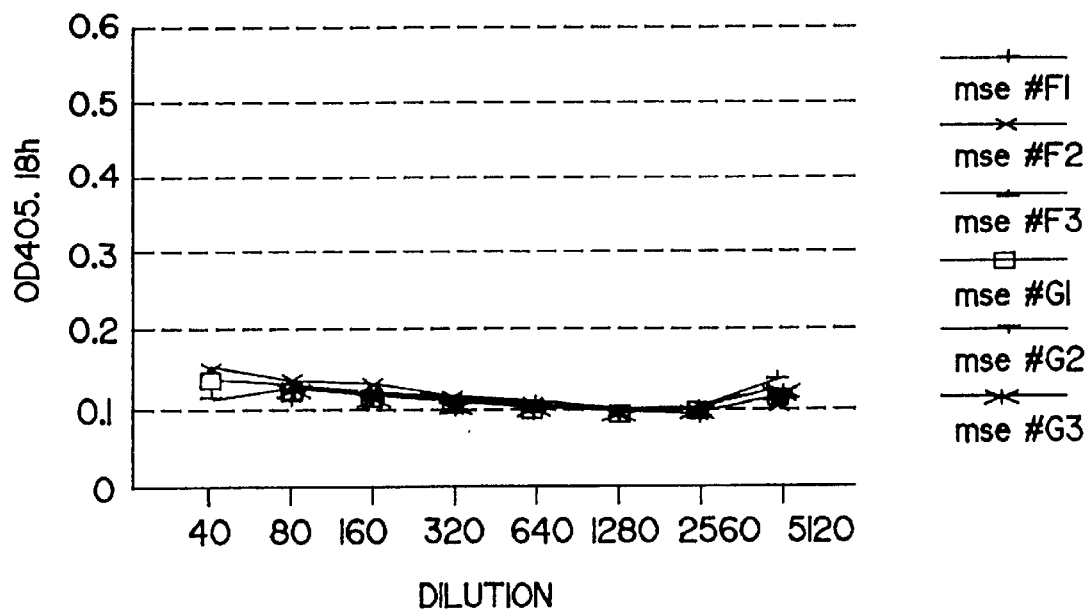
FIG. 3 depicts the results of an ELISA for anti-NP IgG before intranasal introduction of naked pCMVRNP to Balb/c mice.

FIG. 3 graphically depicts the results of the ELISA assays before and after intranasal introduction of the plasmid. The graphs plot ELISA titer against serum dilution. In FIG. 3, values are shown for individual mice from each group (#1–3) and an average value from all mice in each group (#G1–G3).

Figure 4:
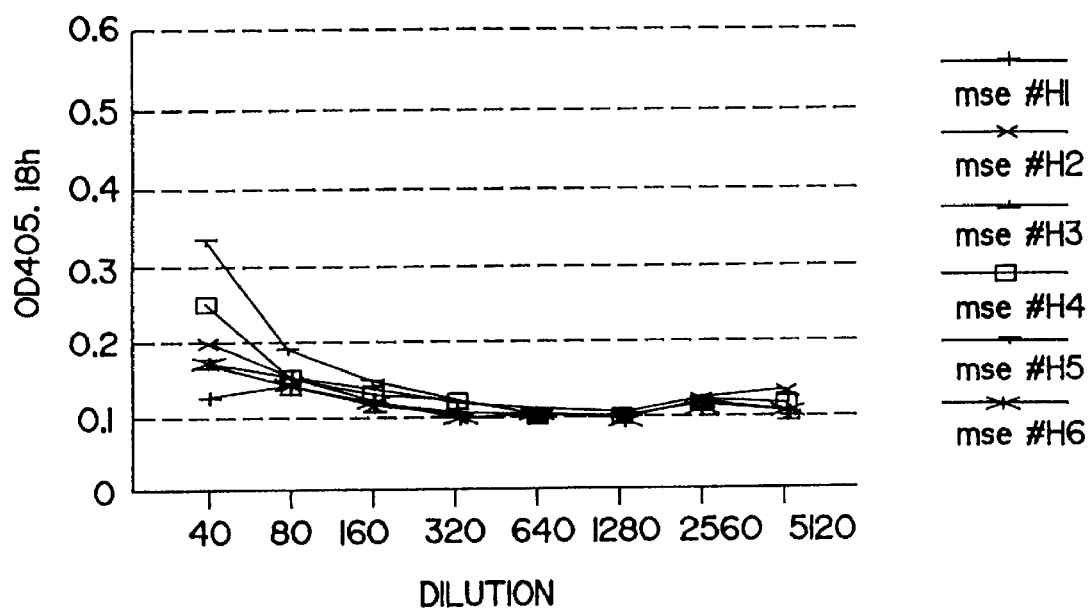
FIG. 4 depicts the results of an ELISA for anti-NP IgG in an unanesthesized group of Balb/c mice.

Without anesthesia, mice in a second group which received 3×7.5 µg of plasmid showed enhanced titers of antibody as compared to background (FIG. 3). These data are shown in FIG. 4.

Figure 5:
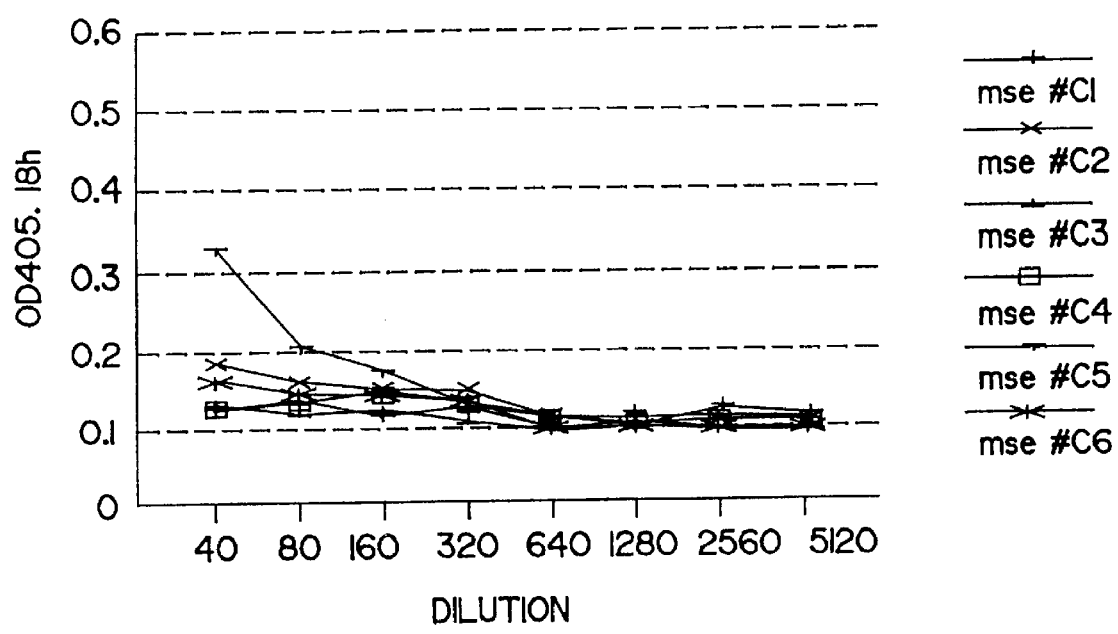
FIG. 5 depicts the results of an ELISA for anti-NP IgG in an anesthesized group of Balb/c mice.

A third group of mice received the same gravity of plasmid under anesthesia. Expression of RNP as indicated by titers of anti-NP IgG in these mice was substantially similar to the expression achieved in the unanethesized mice. The data for the anethesized mice are shown in FIG. 5.

Expression can be enhanced by additional use of absorption promoters, and prolonged by time-released promoters whose identity and use are known in the art such as those suggested in Chien, supra, at Ch. 5.

EXAMPLE IV

HISTOLOGICAL STUDIES SHOWING CELL UPTAKE OF NAKED POLYNUCLEOTIDES BY MONONUCLEAR CELLS AT THE POINT OF ENTRY IN SKIN

Three days after intradermal injection of the tails of naked pCMV/acz into Balb/c mice, the mice were sacrificed. Tissue cultures were obtained at the point of entry for the plasmid and stained for *E. coli* β-galactosidase activity. A photograph (40× magnification) of a slide from the histological examination of these cultures is contained in FIG. 6.

Figure 6:
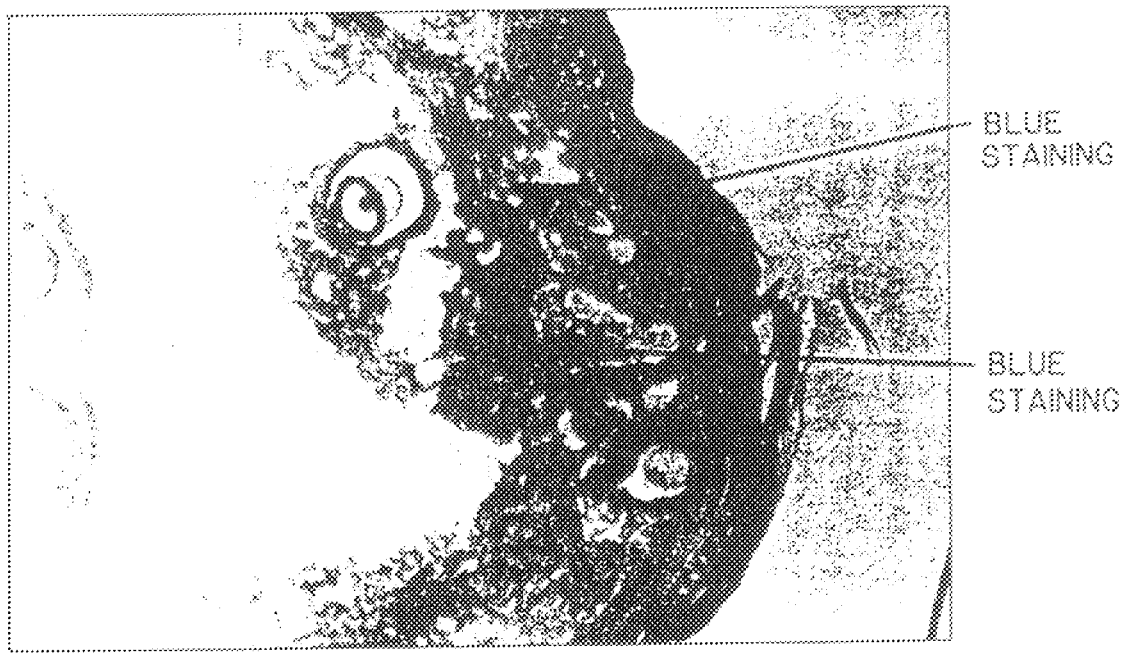
FIG. 6 is a photograph of the results of histological studies of skin at the point of entry for pCMVRNP in Balb/c mice showing uptake of the plasmid by mononuclear cells (APC's). An APC is indicated by an arrows; a tissue cell (not containing the plasmid) is indicated by a slashed line.

As shown in FIG. 6, uptake of the plasmid is shown (in blue) to be by mononuclear cells. The fibroblasts in the tissue samples are not stained, thus indicating that the plasmid was not taken up by these cells. The rounded, mononuclear cells which did take up the plasmid appear to be macrophages and/or other antigen presenting cells, which would indicate that uptake of the plasmid is by phagocytosis.

EXAMPLE V

EPIDERMAL ADMINISTRATION OF A NAKED POLYNUCLEOTIDE USING A MECHANICAL IRRITANT TO ELICIT AN IMMUNE RESPONSE

Figure 7:
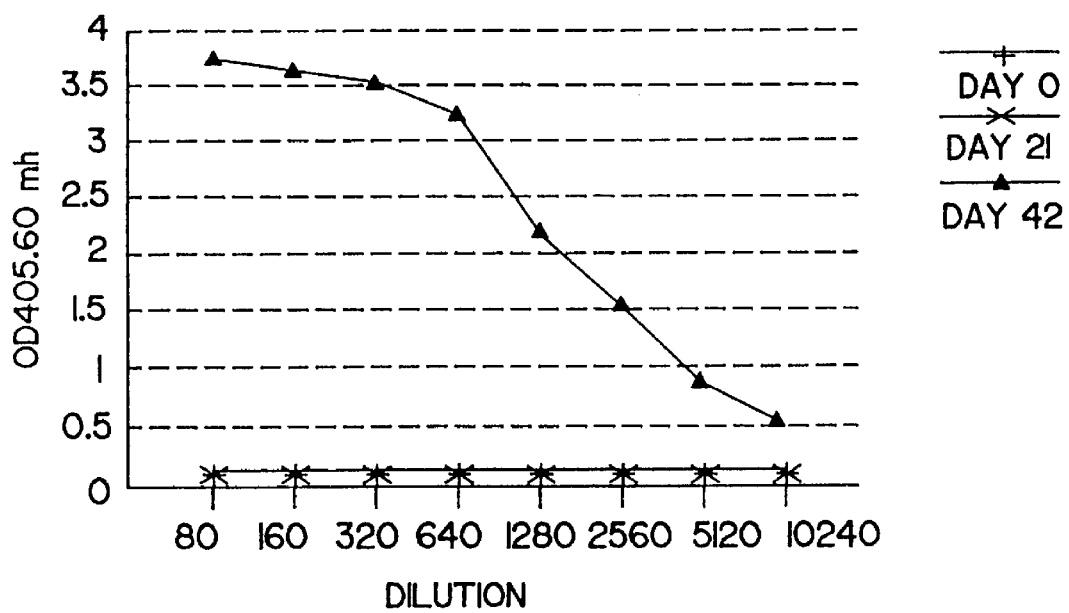
FIG. 7 depicts the results of an ELISA for anti-NP IgG following mechanical epidermal administration of naked pCMVRNP to Balb/c mice.

FIG. 7 depicts the results of an ELISA performed as described in Example I for serum levels of anti-NP IgG following epidermal administration of pCMVRNP via mechanical means.

The plasmid was coated onto the tynes of an uncoated MONO-VACC® device as described supra. (It should be noted that it is alternatively possible for the naked polynucleotides to be lyophilized onto the tynes of the device for longer storage stability). Total plasmid concentration on all of the device tynes was approximately 50 µg in an isotonic normal saline carrier (approximately 150 µg plasmid per milliliter). The back of a Balb/c mouse was shaved and the shaved skin gently scratched with the tyne device. As shown in FIG. 7, anti-NP IgG were subsequently detected in serum (e.g., at day 42, the serum from this mouse contained antibodies at a titer of 1:10240).

EXAMPLE VI

EPIDERMAL ADMINISTRATION OF A NAKED POLYNUCLEOTIDE USING A CHEMICAL AGENT TO ELICIT AN IMMUNE RESPONSE

Figure 8:
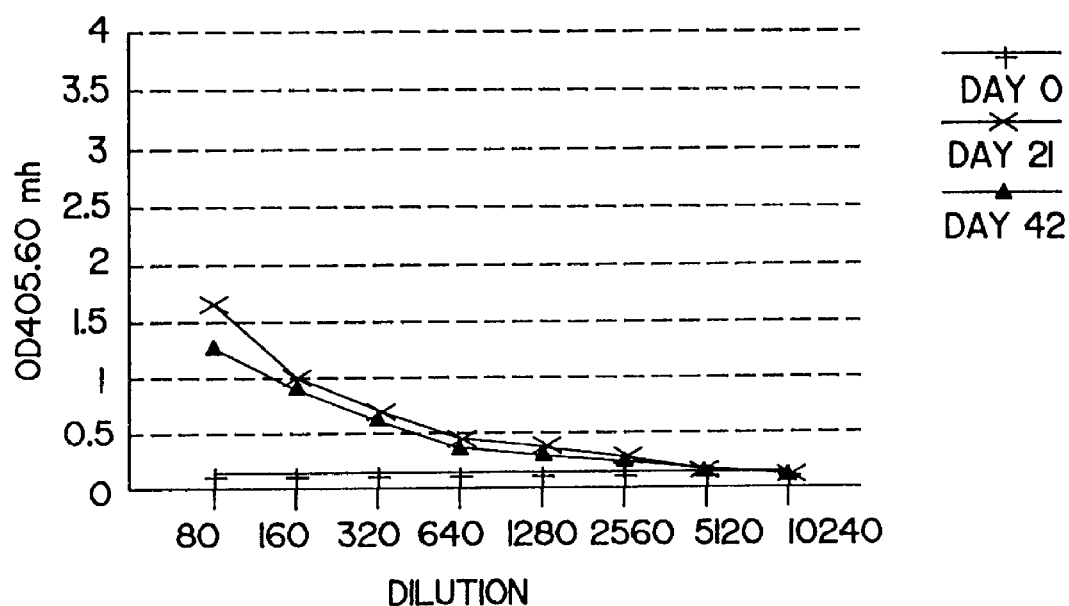
FIG. 8 depicts the results of an ELISA for anti-NP IgG following chemical epidermal administration of naked pCMVRNP to Balb/c mice.

FIG. 8 depicts the results of an ELISA performed as described in Example I for serum levels of anti-NP IgG following epidermal administration of pCMVRNP in conjunction with the application of a chemical agent.

The plasmid was suspended in 40 $\mu$g of an isotonic normal saline solution containing approximately 150 $\mu$g of plasmid per milliliter. This solution was absorbed onto the nonadhesive pad of a BAND-AID brand bandage (Johnson & Johnson).

A Balb/c mouse was shaved as described in Example V and a commercially available keratinolytic agent (here, the previously described depilatory creme sold under the tradename NAIR) was applied to the shaved skin. After several minutes, the keratinolytic agent was washed off of the skin and the plasmid-containing bandage applied thereto. As shown in FIG. 8, the treated animal developed serum anti-NP IgG at a titer of 1:640.

EXAMPLE VII

IMMUNE RESPONSE TO VIRAL CHALLENGE BY MICE INTRADERMALLY INJECTED WITH NAKED pCMVRNP

To test whether immunity generated by vaccination with appropriate naked polynucleotides could protect animals from a lethal viral challenge, groups of 10 Balb/c mice were injected intradermally 3 times with 15 $\mu$g of a pCMVRNP plasmid which contained the NP gene from an H1N1 strain of influenza virus (A/PR/8/34; provided by Dr. Inocent N. Mbawvike at the Baylor College of Medicine, U.S.) Control groups included uninjected animals as well as animals injected with an irrelevant plasmid (pnBL3).

Figure 9:
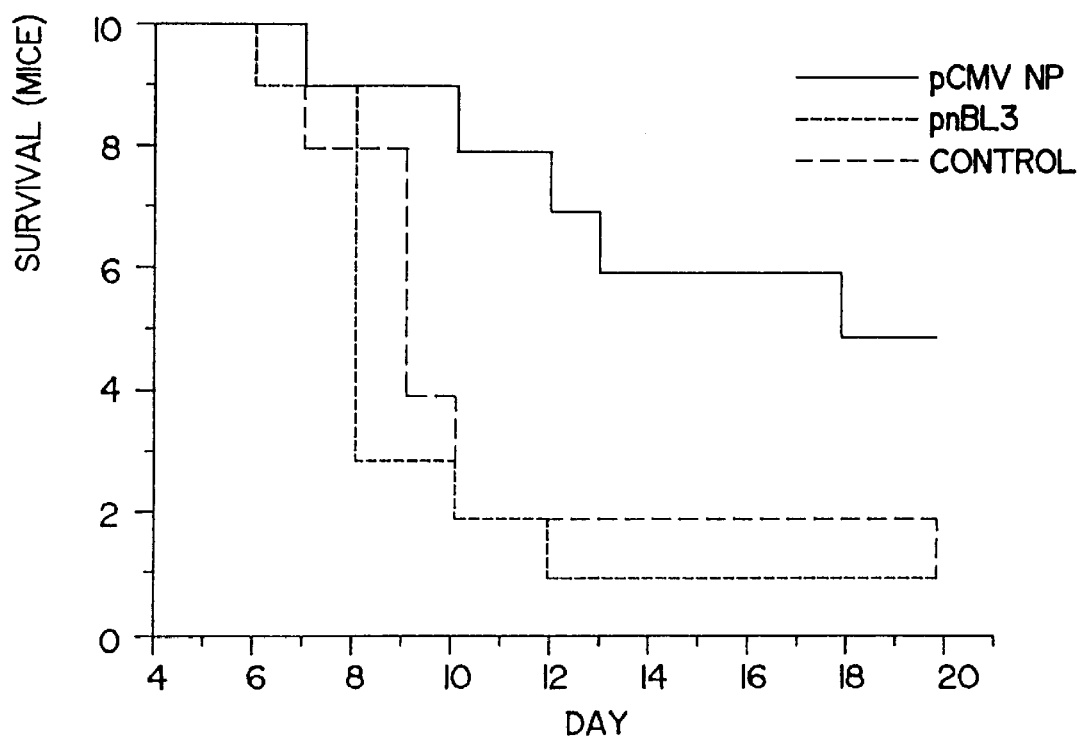
FIG. 9 contains a Kaplan-Meyer survival curve depicting the length of time that Balb/c mice injected intradermally with naked pCMVRNP survived following viral challenge.

Six weeks after the initial plasmid injections, the animals were challenged with a $LD_{90}$ dose of an H3N2 influenza strain (A/HK/68); also provided by Dr. Mbawuike). Intradermally vaccinated mice were significantly protected from the challenge (P(0.01) as compared to unvaccinated control mice; see, FIG. 9 (a Kaplan-Meyer survival curve).

EXAMPLE VIII

RELATIVE LEVELS OF GENE EXPRESSION FOLLOWING INTRADERMAL INJECTIONS OF NAKED CYTOMEGALOVIRUS OR ROUS SARCOMA VIRUS PROMOTER-CONTAINING NAKED PLASMIDS

Figure 10:
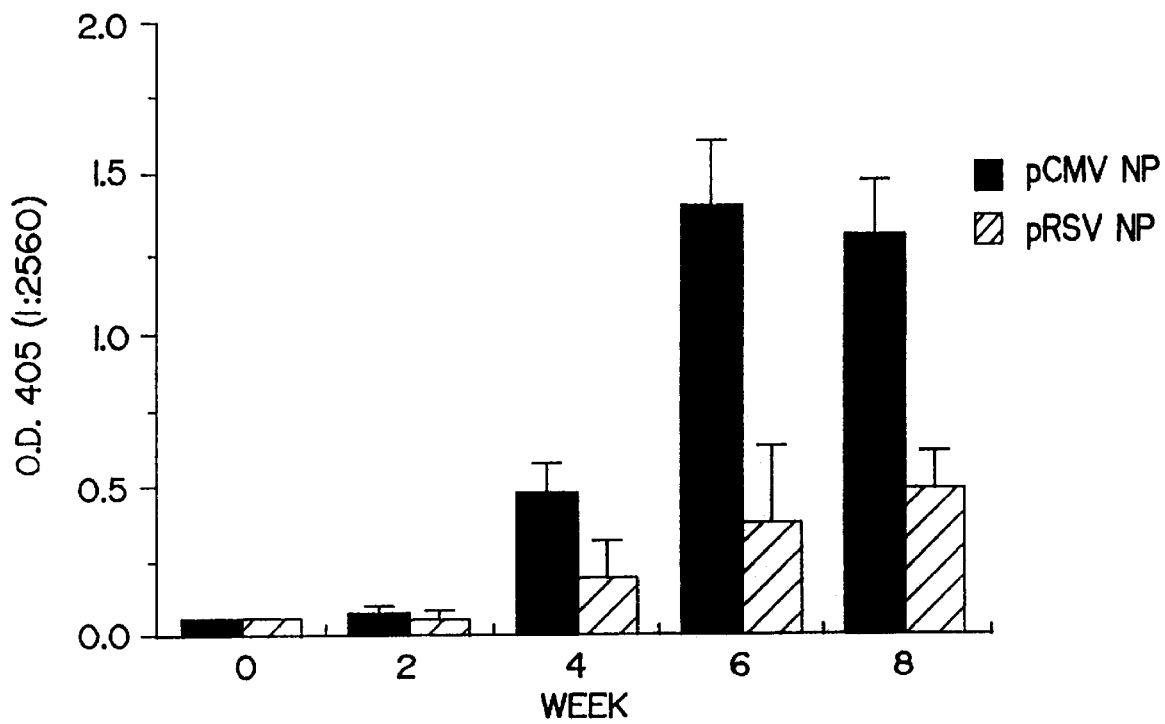
FIG. 10 graphically compares NP gene expression following separate intradermal injections of naked plasmids containing either a CMV or an RSV promoter sequence.

The possible effect of the promoter region used in an expression vector was evaluated by testing two plasmids which contain the RNP gene described in Example II. One plasmid, pCMVRNP, contained the cytomegalovirus immediate early promoter, enhancer and intron region. The other plasmid contained the promoter from the Rous sarcoma virus LTR region (pRSVRNP). As shown in FIG. 10, antibody responses to the NP protein expressed by the plasmids were consistently higher with the CMV promoter after intradermal injections. This contrast with the responses seen after intramuscular injection of the NP gene, where antibody levels produced by the two plasmids are essentially equivalent (data not shown).

EXAMPLE IX

SELECTIVE INDUCTION OF CYTOTOXIC T LYMPHOCYTE RESPONSES AFTER INTRADERMAL ADMINISTRATION OF NAKED POLYNUCLEOTIDES

Mice of the C57/B6 strain were injected intradermally in the tail at two week intervals with 100 $\mu$g naked DNA purified from a CDM8 ova plasmid (described in detail in Shastri, et al., *J. Immunol.*, 150:2724–2736, 1993). The CDM8 ova plasmid contains the full length (1.8 kb) cDNA for ovalbumin.

2 weeks after the second gene adminstration, the spleens of the mice wre removed and cultured in vitro with lethally irradiated (3000 rad) syngeneic splenocytes that had been pulsed with a synthetic ovalbumin peptide. This peptide is a class I restricted target for cytotoxic T cells in mice with the histocompatibility haplotype $K^b$ described by Shastri, et al.

After five days of culture, the cells were incubated with targets of 2 types to test for the generation of cytotoxic T cells by the mice who had received the gene encoding ovalbumin. The targets were mouse EL-4 lymphocytes pulsed with the synthetic ovalbumin peptide, or EL-4 cells that had been stably transfected with the cDNA for ovalbumin (see, FIG. 11; the cDNA for ovalbumin is designated as "EG7" in the FIGURE). The percent lysis of the 2 targets was determined for different effector-to-target ratios (designated as "E:T ratio" in FIG. 11). As shown in FIG. 11, the animals that received the naked CDM8 ova plasmid had produced cytotoxic T cells that were specific for the ovalbumin targets (i.e., for EL-4 with the ovalbumin peptide and for EG7), but were not specific for the control EL-4 cells (i.e., those without the ovalbumin peptide).

Figure 12:
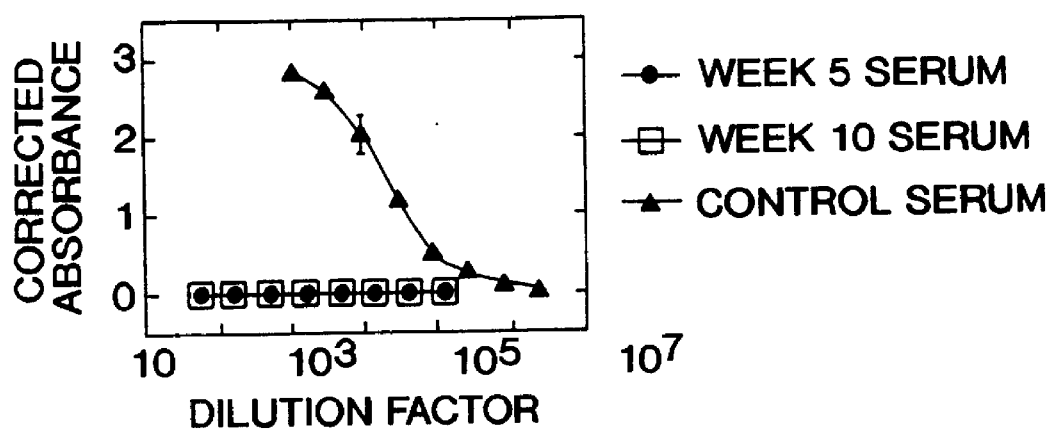
FIG. 12 depicts the results of an ELISA for anti-ovalbumin antibodies in the mice described with respect to FIG. 11.

C57/B6 mice vaccinated intradermally with CDM8 ova plasmids were also screened for antibodies to ovalbumin. Sera collected 6 weeks after administration of the CDM8 ova plasmids did not contain any detectable levels of antibody (as measured using an enzyme-linked immunoabsorbent assay on microtiter plates coated with ovalbumin; see, FIG. 12). Collectively, these data indicate that the methods for administration of naked polynucleotides of the invention will induce MHC class I restricted cytotoxic T cells (here, to ovalbumin) without inducing antibody production.

EXAMPLE X

PROLONGED IMMUNOLOGIC MEMORY AFTER INTRADERMAL ADMINISTRATION OF NAKED POLYNUCLEOTIDES INDUCED BY ANTIGEN STIMULATION OF T CELLS 0.1, 1, 10 and 100 $\mu$g of naked polynucleotides in plasmid form (0.5–5 ng/1 mg DNA endotoxin content) encoding the *E. coli* enzyme β-galactosidase under the control of the CMV promoter ("pCMV Lac-Z") were administered to groups of 4 mice\dosage\route either intramuscularly ("IM") or intradermally ("ID"). For comparison, another group of 4 mice\dosage received 100 $\mu$g β-galactosidase protein ("PR") intradermally. All injections were made using 50 $\mu$l normal saline as carrier. IM and ID injections were made with a 0.5 ml syringe and a 28.5 gauge needle. Antibodies were thereafter measured by enzyme-linked immunoabsorbent assay at 2 week intervals.

Briefly, total antibodies were measured using β-galactosidase (Calbiochem, California) as the solid phase antigen. Microtiter plates (Costar, Cambridge, Mass.) were coated with 5 μg of antigen dissolved in 90 mM borate (pH 8.3) and 89 mM NaCl (i.e., borate buffered saline; BBS) overnight at room temperature and blocked overnight with 10 mg/ml of bovine serum albumin in BBS.

Serum samples were serially diluted in BBS starting at a 1:40 dilution for the first 8 weeks, them a 1:320 dilution thereafter. These samples were added to the plates and stored overnight at room temperature. Plates were washed in BBS+ 0.05% polysorbate 20, then reacted with a 1:2000 dilution of alkaline phosphatase labeled goat anti-mouse IgG antibody (Jackson Immunoresearch Labs., West Grove, Pa.) for 1 hour at room temperature, or were reacted with a 1:2000 dilution of alkaline phosphatase labeled goat anti-mouse IgG 1 antibody (Southern Biotech of Alabama), or were reacted with a 1:500 dilution of alkaline phosphatase labled rat anti-mouse IgG 2A antibody (Pharmingen, of California), under the same conditions. Plates were washed again, then a solution of 1 mg/ml of p-nitrophenol phosphate (Boehringer-Mannheim, Indianapolis, Ind.) in 0.05M carbonate buffer (pH 9.8), containing 1 mM $MgCl_2$ was added. Absorbance at 405 nm was read 1 hour after addition of substrate to the plates.

Figure 13:
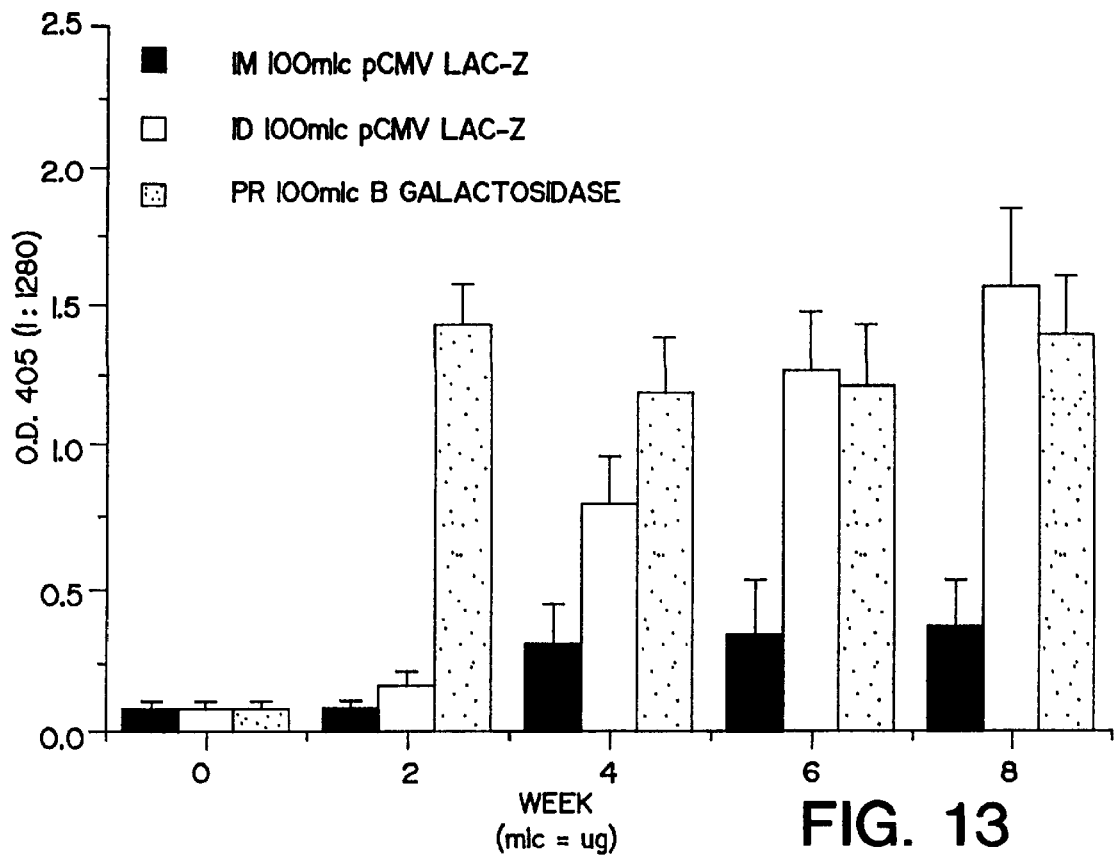
FIG. 13 depicts the results of an ELISA for anti-β-galactosidase antibodies after administration of (1) a polynucleotide encoding the enzyme by intramuscular or intradermal injection, and (2) the enzyme by intradermal injection.

As shown in FIG. 13, antibody responses of equivalent magnitude were induced in the animals who had received the pCMV Lac-Z plasmids by ID injection and the amimals who had received the PR, while lesser antibody responses were measured in the animals who had received the pCMV Lac-Z plasmids by IM injection.

To assess for T cell memory, the animals were then boosted with 0.5 μg of PR at a separate site by ID injection. If these animals had developed memory T cells to control production of antibody to β-galactosidase, they would be expected to mount a more vigorous immune response after boosting with soluble protein antigen than had been demonstrated in response to the priming dose of antigen.

Figure 14:
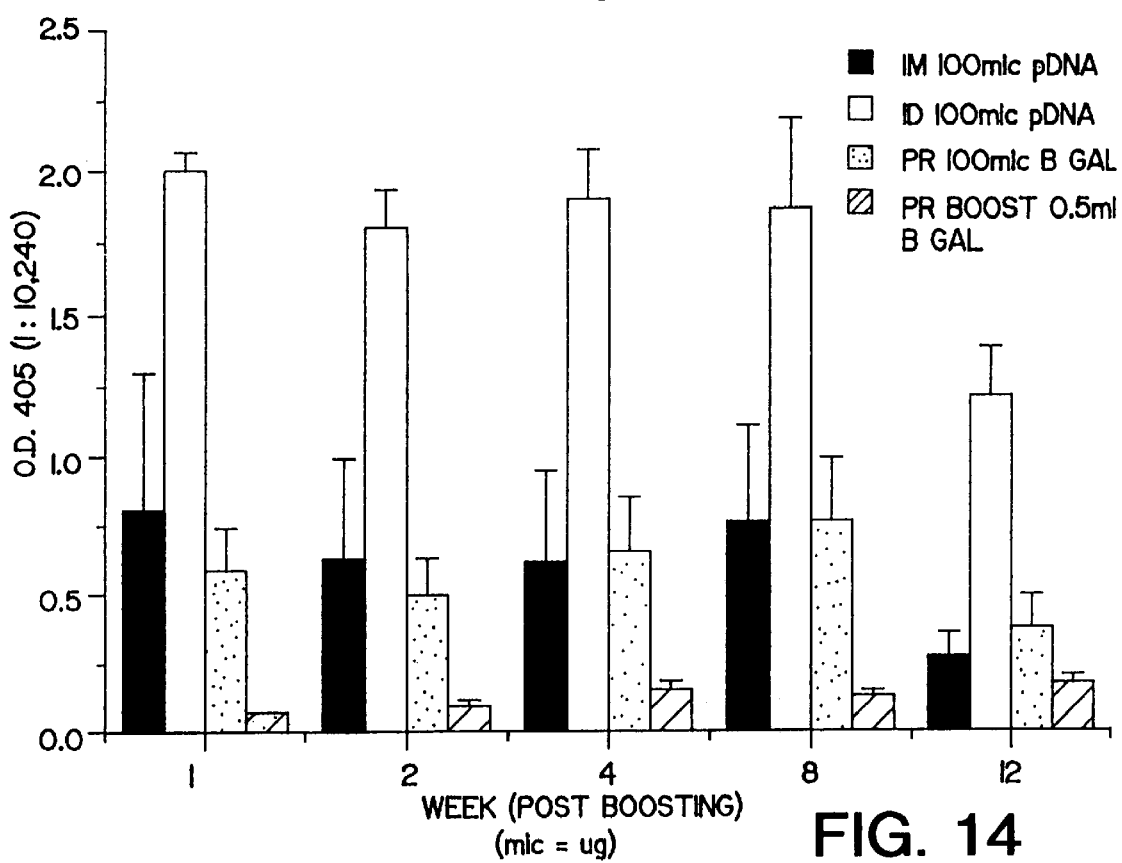
FIG. 14 depicts the results of an ELISA for anti-β-galactosidase antibodies in sera from the mice described with respect to FIG. 22 after a booster injection of antigen.

As shown in FIG. 14, it is clear that the animals which had received ID injections of pCMV Lac-Z plasmid had developed substantially better immunological memory than did animals which had received either IM injections of plasmid or of PR. Further, the memory which was developed by the ID injected animals persisted for a minimum of about 12 weeks.

EXAMPLE XI

SELECTIVE INDUCTION OF A TH1 RESPONSE AFTER INTRADERMAL ADMINISTRATION OF NAKED POLYNUCLEOTIDES

In mice, IgG 2A antibodies are serological markers for a TH1 type immune response, whereas IgG 1 antibodies are indicative of a TH2 type immune response. TH2 responses include the allergy-associated IgE antibody class; soluble protein antigens tend to stimulate relatively strong TH2 responses. In contrast, TH1 responses are induced by antigen binding to macrophages and dendritic cells. TH1 responses are to be of particular importance in the treatment of allergies and AIDS.

To determine which response, if any, would be produced by mice who received naked polynucleotides according to the invention, mice were vaccinated with pCMV Lac-Z or protein as described in the preceding example. At 2 week intervals, any IgG 2a and IgG 1 to β-galactosidase were measured by enzyme-linked immunoabsorbent assay (using antibodies specific for the IgG 1 and IgG 2A subclasses) on microtiter plates coated with the enzyme.

Figure 15:
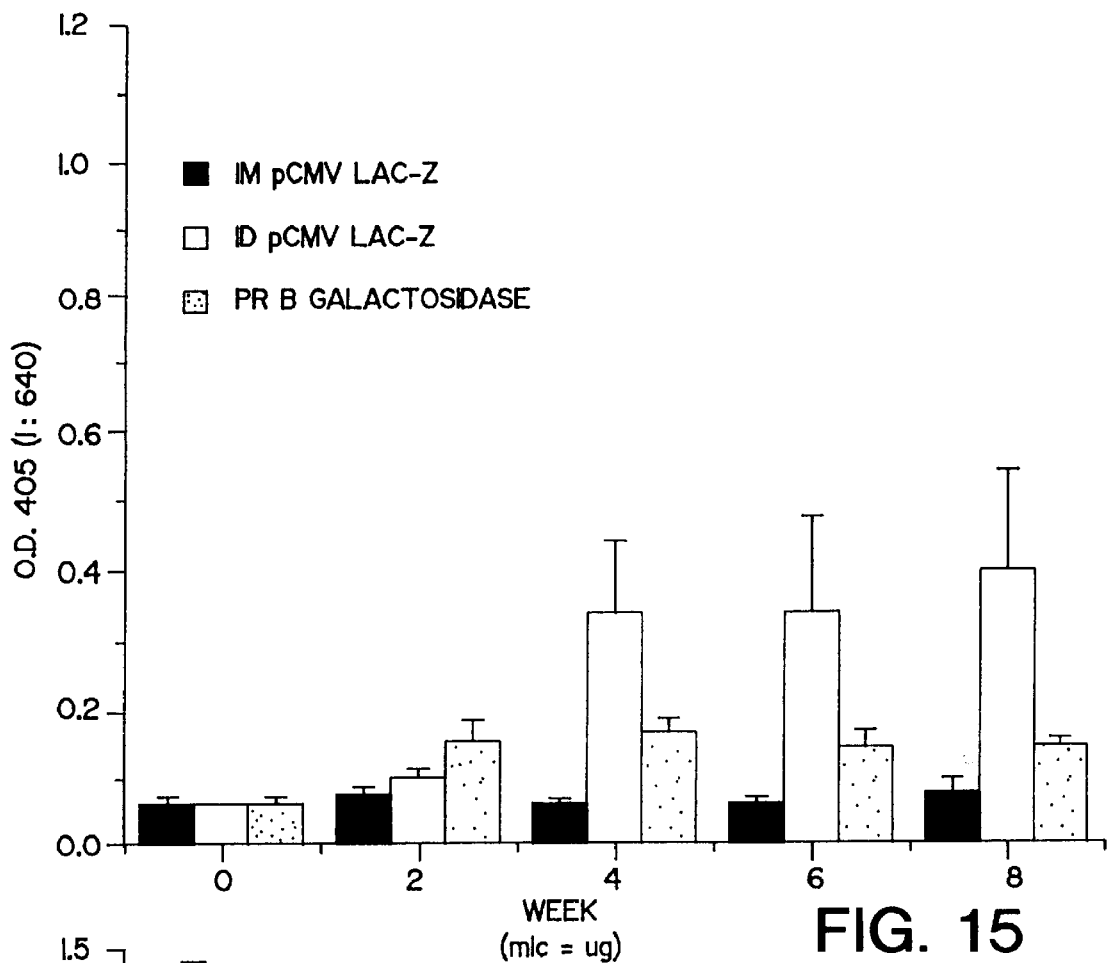
FIG. 15 depicts the results of an ELISA for IgG 2A type antibodies in sera for mice (1) injected intradermally or intramuscularly with a polynucleotide encoding β-galactosidase, or (2) the enzyme by intradermal injection.
Figure 16:
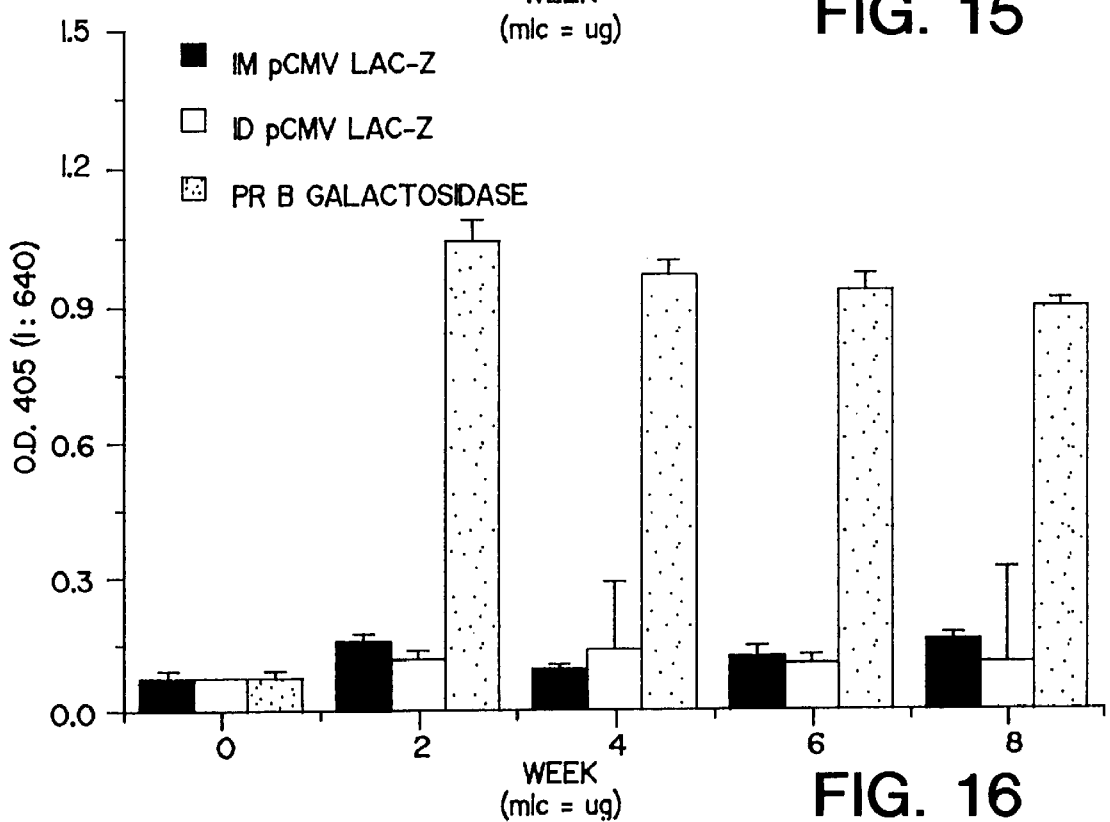
FIG. 16 depicts the results of an ELISA for IgG 1 type antibodies in sera for mice (1) injected intradermally or intramuscularly with a polynucleotide encoding β-galactosidase, or (2) the enzyme by intradermal injection.

As shown in FIG. 15, only the mice who received the plasmid by ID injection produced high titers of IgG 2A antibodies. As shown in FIG. 16, immunization of the mice with the enzyme itself ("PR") induced production of relatively high titers of IgG 1 antibodies. In the IM injected mice, low titers of both IgG 2A and IgG 1 antibodies were produced without apparent selectivity. The data shown in the FIGURES comprise averages of the values obtained from each group of 4 mice.

Figure 17:
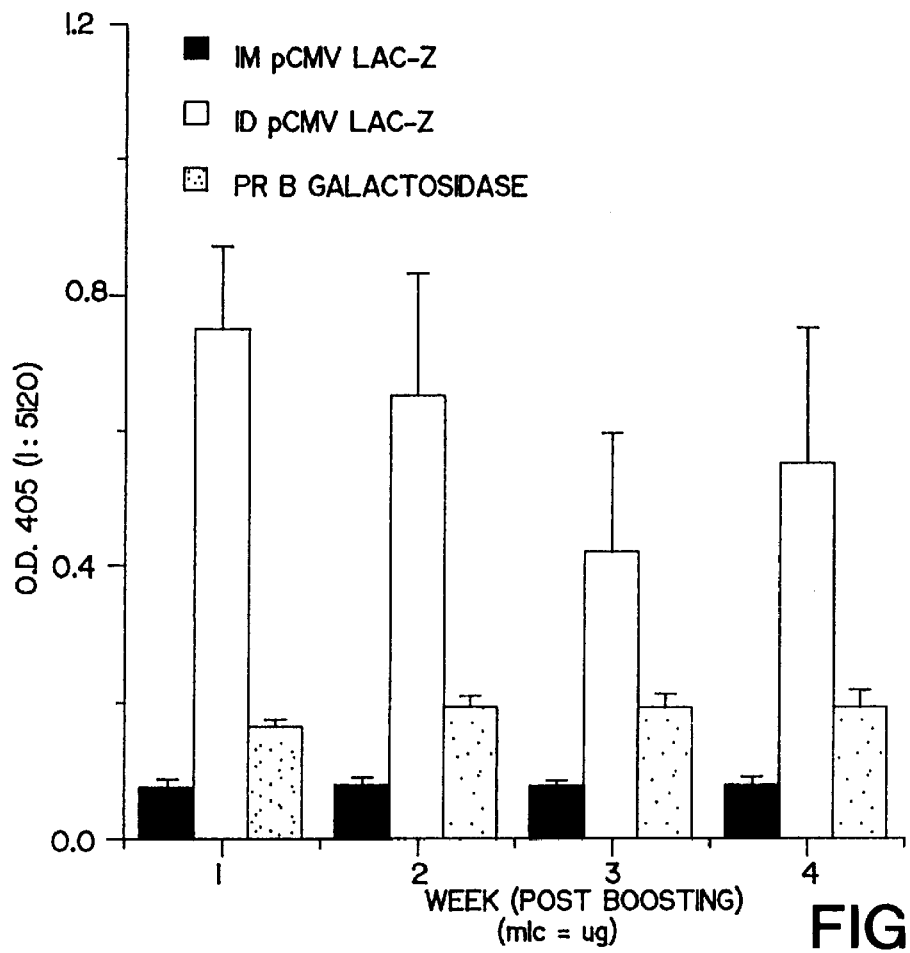
FIG. 17 depicts the results of an ELISA for IgG 2A type antibodies in sera of the mice described with respect to FIG. 25 after a booster injection of antigen.
Figure 18:
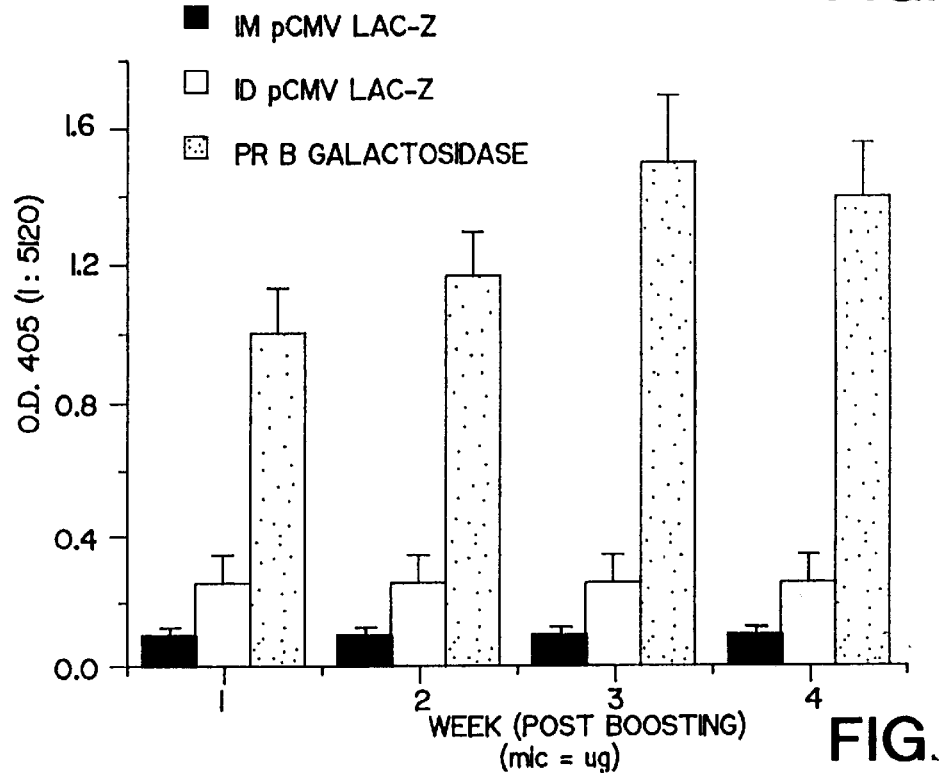
FIG. 18 depicts the results of an ELISA for IgG 1 type antibodies in sera of the mice described with respect to FIG. 24 after a booster injection of antigen.

To determine the stability of the antibody response over time, the same group of animals were boosted with 0.5 μg of enzyme injected intradermally. As shown in FIGS. 17 and 18 boosting of ID injection primed animals with the enzyme induced a nearly 10-fold rise in IgG 2A antibody responses (i.e., the antibody titer rose from 1:640 to 1:5120), but did not stimulate an IgG 1 response. These data indicate that the selective TH1 response induced by ID administration of naked polynucleotides is maintained in the host, despite subsequent exposure to antigen.

EXAMPLE XII

TH1 RESPONSES IN MICE AFTER ADMINISTRATION OF NAKED POLYNUCLEOTIDES WITH A MECHANICAL IRRITANT

The experiments described in Example XI were repeated in separate groups of mice, except that (1) only a priming dose was tested, and (2) the pCMV Lac-Z plasmid was administered to one group of 4 mice using the tyne device described in Example V, while -galactosidase protein (10 μg) was administered to another group of 4 mice by intradermal (ID) injection.

Figure 19:
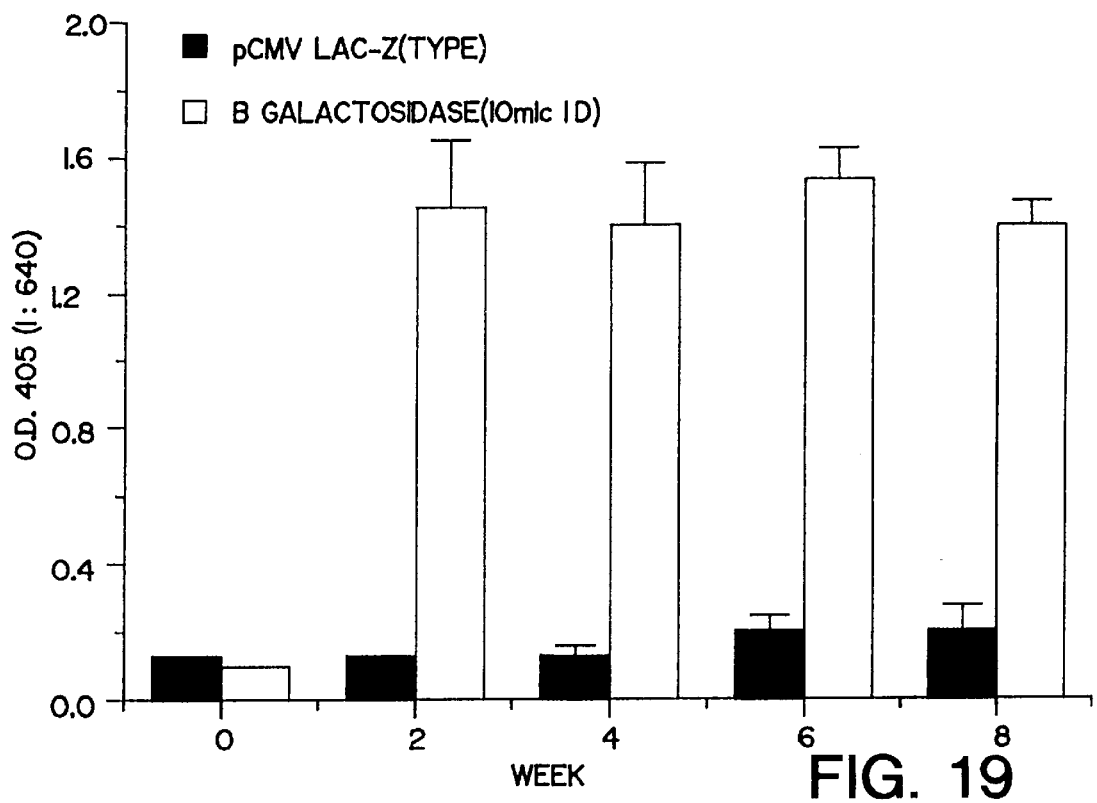
FIG. 19 depicts the results of an ELISA for IgG 2A type antibodies in sera for mice (1) introduced by scratching the skin with tynes coated with a polynucleotide encoding β-galactosidase, or (2) the enzyme by intradermal injection.
Figure 20:
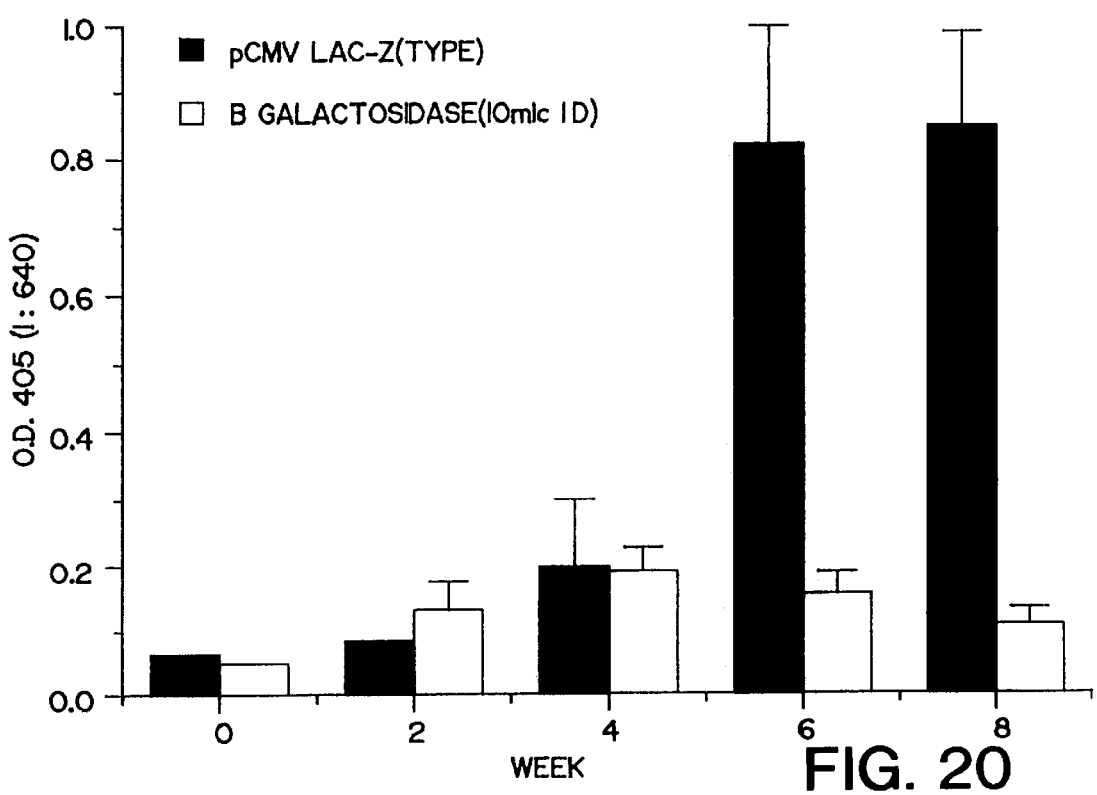
FIG. 20 depicts the results of an ELISA for IgG 1 type antibodies in sera for mice (1) introduced by scratching the skin with tynes coated with a polynucleotide encoding β-galactosidase, or (2) the enzyme by intradermal injection.

As shown in FIG. 19, the mice who received plasmid produced relatively low titers of IgG 1 antibody compared to the mice who received the protein. In contrast, as shown in FIG. 20, the mice who received plasmid produced substantially higher titers of IgG 2A antibody as compared to the mice who received the protein.

These results are similar to those obtained in Example XI except that, interestingly, the mice who received the plasmid via scratching of their skin with the tyne device produced even higher titers of IgG 2A antibody than did the mice who received the same plasmid via ID injection (both of which groups produced higher titers of IgG 2A antibody than did the mice who received the plasmid via IM injection). These results indicate that scratching of skin with the tyne device attracts greater number of APC's to the "injured" point of entry for the naked polynucleotides and are consistent with the theory that APC's are more efficient targets for gene administration and expression than are muscle or other somatic cells.

The data shown in the FIGURES comprise averages of the values obtained from each group of 4 mice.

EXAMPLE XIII

SUPPRESSION OF IgE ANTIBODY RESPONSE TO ANTIGEN BY IMMUNIZATION WITH ANTIGEN-ENCODING POLYNUCLEOTIDES

Using the experimental protocol described in Example XI, five to eight week old Balb/c mice were immunized with one of two recombinant expression vectors: pCMV-Lac-Z (described in Example X) or a control plasmid, pCMV-BL (which does not encode for any insert peptide). A third group of the mice received injections of antigen (β galactosidase). Plasmid DNA was purified and its endotoxin content reduced to 0.5µ5 ng/1 mg DNA by extraction with TRITON X-114 (Sigma, St. Louis, Mich.). Before inoculation, pDNA was precipitated in ethanol, washed with 70% ethanol and dissolved in pyrogen free normal saline.

Immunization was by intradermal injection of plasmid DNA loaded onto separate tynes of a MONOVACC® multiple tyne device (Connaught Lab, Inc., Swiftwater, Pa.). Briefly, the tyne devices were prepared after extensive washing in DDW and overnight soaking in 0.5% SDS (sulfated dodecyl saline), washed again in DDW, soaked overnight in 0.1N NaOH, washed again in DDW and dried at 37° C. for 8 hours. Six µl of plasmid DNA dissolved in normal saline were pipetted onto the tynes of the tyne device just prior to each inoculation described below. The total amount of pDNA loaded on the device per inoculation was 25 µg each of pCMV-Lac-Z and PCMV-BL. For purposes of estimating actual doses, it was assumed that less than 10% of the pDNA solution loaded onto the tyne device was actually introduced on injection of the tynes into intradermal tissue.

Each mouse was treated 3 times with 2 inoculations of each plasmid in a one week interval injected intradermally at the base of the tail. Another group of mice received a single intradermal injection in the base of the tail of 10 µg of β galactosidase protein (dissolved in 50 µl of normal saline) in lieu of pDNA.

Toward inducing an IgE antibody response to subsequent allergen challenge, each group of mice was injected once intraperitoneally with 0.1 ml of phosphate buffered saline (PBS) solution containing 1 µg of antigen (β galactosidase; Calbiochem, San Diego, Calif.) and 3mg of ALUM aluminum hydroxide as adjuvant (Pierce Chemical, Rockford, Ill.) 14 weeks after the initial immunization. Total IgE was assayed in sera from the mice 4 times over the subsequent 4 consecutive weeks.

IgE was detected using a solid phase radioimmunoassay (RAST) in a 96 well polyvinyl plate (a radioisotopic modification of the ELISA procedure described in Coligan, "Current Protocols In Immunology", Unit 7.12.4, Vol. 1, Wiley & Sons, 1994), except that purified polyclonal goat antibodies specific for mouse ε chains were used in lieu of antibodies specific for human Fab. To detect anti-Lac-Z IgE, the plates were coated with β galactosidase (10 µg/ml). The lowest IgE concentration measurable by the assay employed was 0.4 ng of IgE/ml.

Figure 23:
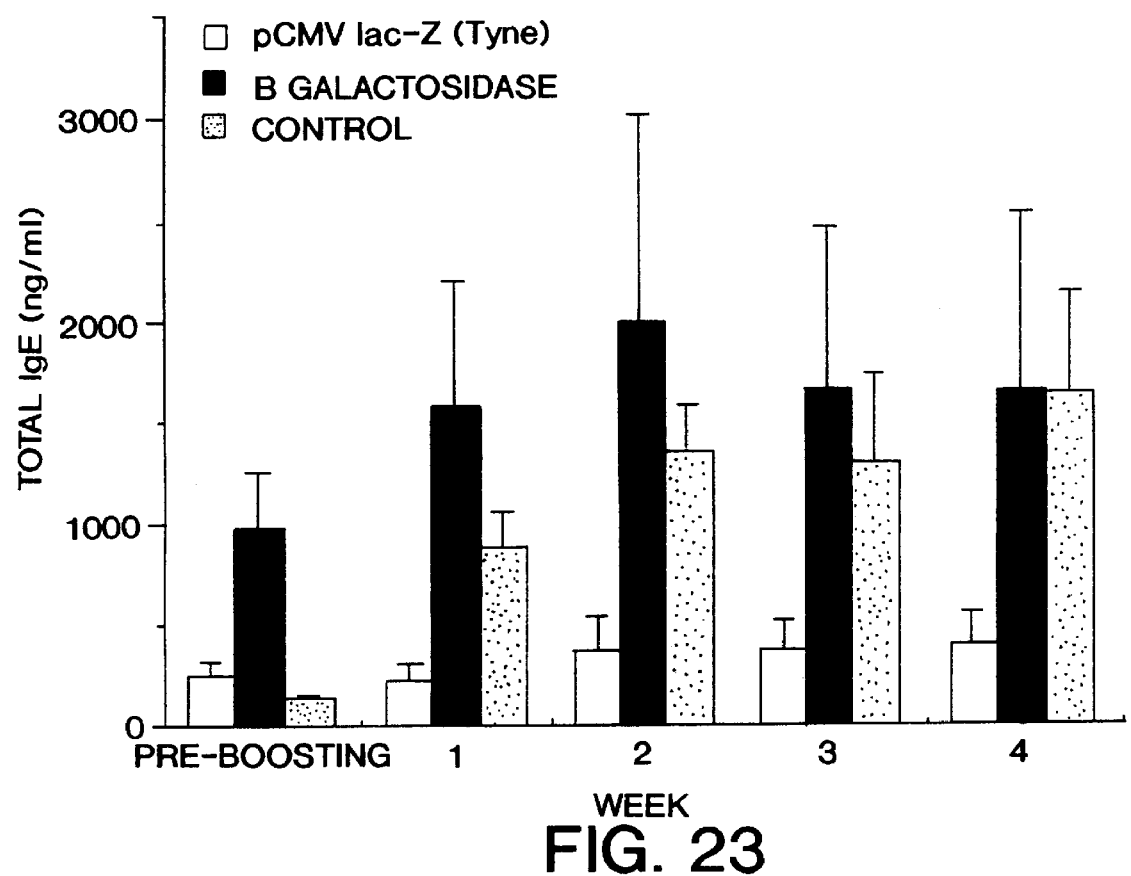
FIG. 23 depicts the results of an ELISA for total IgE antibody levels in mice after immunization with an antigen-encoding plasmid (pCMV-Lac-Z), the antigen itself (β galactosidase), or a control (non-encoding) plasmid (pCMV-BL; "cont.").

As shown in FIG. 23, mice injected with pCMV-Lac-Z produced only low levels of total IgE antibody (averaging about 250 CPM in RAST) as compared to mice injected with β galactosidase (averaging about 1000 CPM in RAST). Moreover, IgE levels in the plasmid injected mice remained consistently low (averaging about 250–450 CPM) despite boosting with protein (indicating that tolerance was acquired in these mice on initial immunization), while IgE levels in the protein injected mice rose substantially (averaging about 1500 to 2000 CPM) after boosting, then eventually tapered off to control levels at week 4 as tolerance was acquired by the protein injected mice through repeated exposure to the protein antigen.

Figure 24:
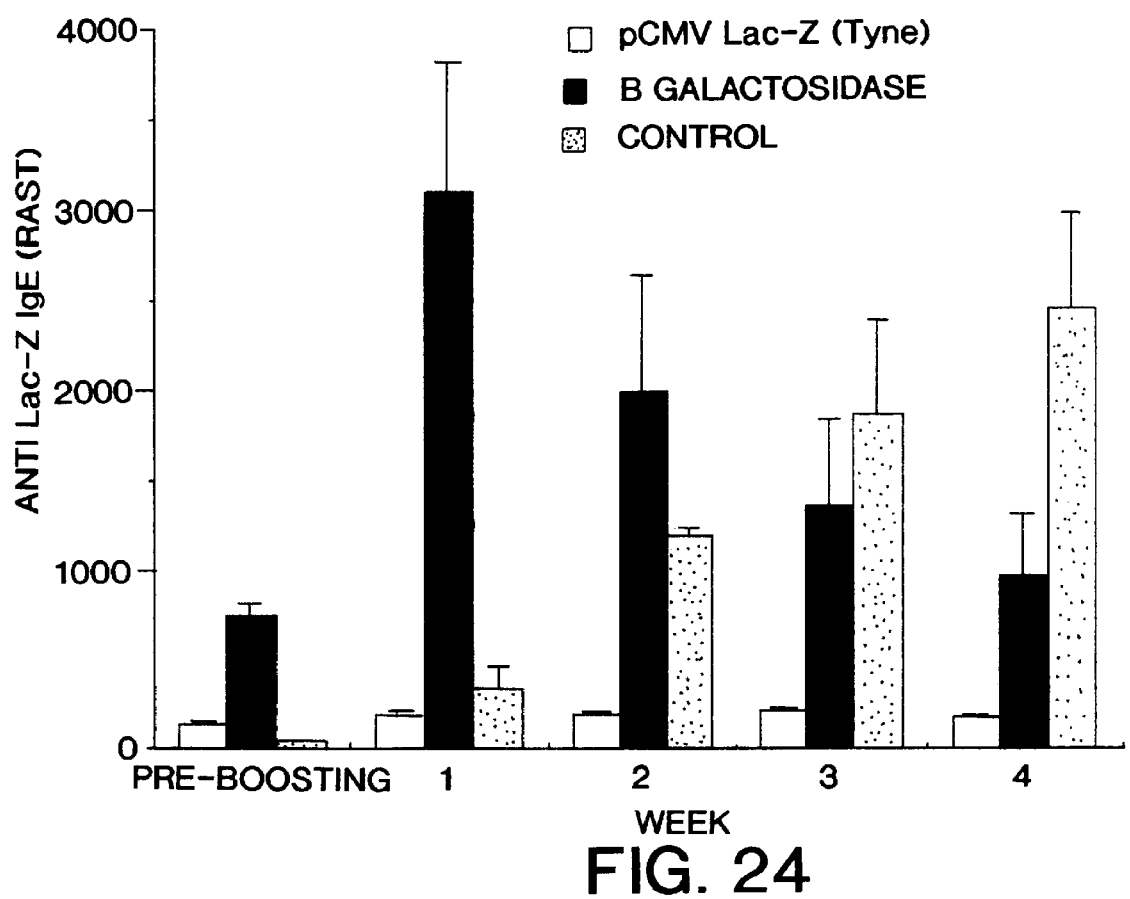
FIG. 24 depicts the results of an ELISA for allergen-specific IgE antibody levels in mice after immunization with an antigen-encoding plasmid (pCMV-Lac-Z), the antigen itself (β galactosidase), or a control (non-encoding) plasmid (pCMV-BL; "cont.").

Measuring specifically the anti-antigen response by each group of mice, as shown in FIG. 24, anti-Lac-Z IgE levels in the plasmid injected mice again were consistently low both before and after boosting (averaging about 250 CPM in RAST), while the protein injected mice developed high levels of anti-Lac-Z, particularly after the first antigen booster injection, when anti-Lac-Z levels in the mice rose to an average of about 3000 CPM. Consistent with acquisition of tolerance, anti-Lac-Z IgE levels in the protein injected mice declined over time, but continued to rise in the control mice who had not received any immunization to β galactosidase.

These data show that the plasmid injected mice developed an antigen specific TH1 response to the plasmid expression product (consistent with the TH1/TH2 response data shown in Examples XI and XII), with concomitant suppression of IgE production, while tolerance was acquired in the protein injected mice only after development of substantially higher levels of total and antigen specific IgE antibodies.

EXAMPLE XIV

IL4 AND INFγ LEVELS IN MICE AFTER IMMUNIZATION WITH ANTIGEN OR ANTIGEN-ENCODING POLYNUCLEOTIDES

To confirm that the results shown by the data presented in Examples XI through XII can be attributed to the selective induction of TH1 responses (e.g., INFγ secretion) in plasmid injected mice (which responses are believed to exert a negative effect on IgE stimulatory TH2 responses; e.g., secretion of IL-2), levels of IL-2 and INFγ were assayed in the sera of the plasmid and protein injected mice of Example XIII at week one, after one booster injection of antigen. IL-2 levels were assayed as described in Example I; INFγ levels were assayed with an anti-INFγ murine antibody assay (see, e.g., Coligan, "Current Protocols in Immunology", Unit 6.9.5., Vol. 1, Wiley & Sons, 1994).

Figure 25:
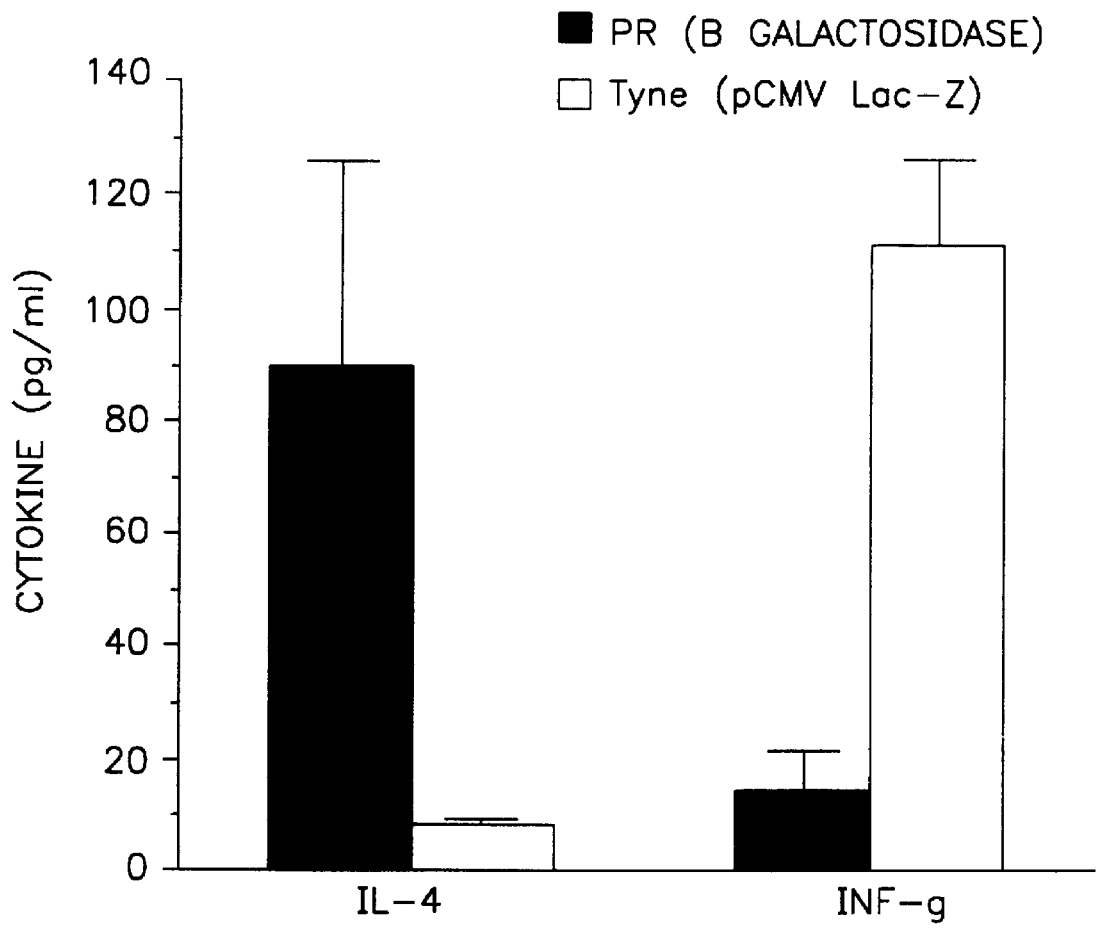
FIG. 25 depicts the results of an ELISA for levels of IL-2 and INFγ after immunization of mice with an antigen-encoding plasmid (pCMV-Lac-Z) or the antigen itself (β galactosidase).

As shown in FIG. 25, levels of IgE stimulatory IL-4 in the protein injected mice were substantially higher than in plasmid injected mice (by about a 9:1 ratio). Conversely, levels of INFγ in the plasmid injected mice were substantially higher than in the protein injected mice (by a ratio of about 11:1).

EXAMPLE XV

PRODUCTION AND MAINTENANCE OF CYTOTOXIC T LYMPHOCYTES AFTER IMMUNIZATION WITH ANTIGEN OR ANTIGEN-ENCODING POLYNUCLEOTIDES

As discussed elsewhere above, it is believed that cytotoxic T lymphocytes (CTLs) suppress TH2 cell activity, which in turn would suppress the ability of such cells to stimulate the development of IgE antibodies. To confirm whether the plasmid injected mice developed CTL's and maintained the anti-antigen protection afforded thereby, CTL levels in plasmid injected and control mice were measured.

The plasmid injected mice were immunized as described in Example XIV, except that they received pCMV-NP (described in Example I) rather than pCMV-Lac-Z. Control mice received pCMV-BL as in Example XIX. The total amount of pDNA loaded on the tyne device per inoculation was 50 µg of pCMV-NP and 25 µg of pCMV-BL.

36 weeks after immunization, the mice were sacrificed and splenocytes were removed for use in standard mixed lymphocyte cultures. The cultures were grown in the presence of a known synthetic peptide representing the major $H-2^d$ restricted CTL epitope of the NP protein. The cultures were assayed for anti-NP CTL activity 5–6 days later using NP peptide pulsed syngeneic P815 tumor cells (ATCC # TIB64, Rockville, Md.) as targets.

Figure 26:
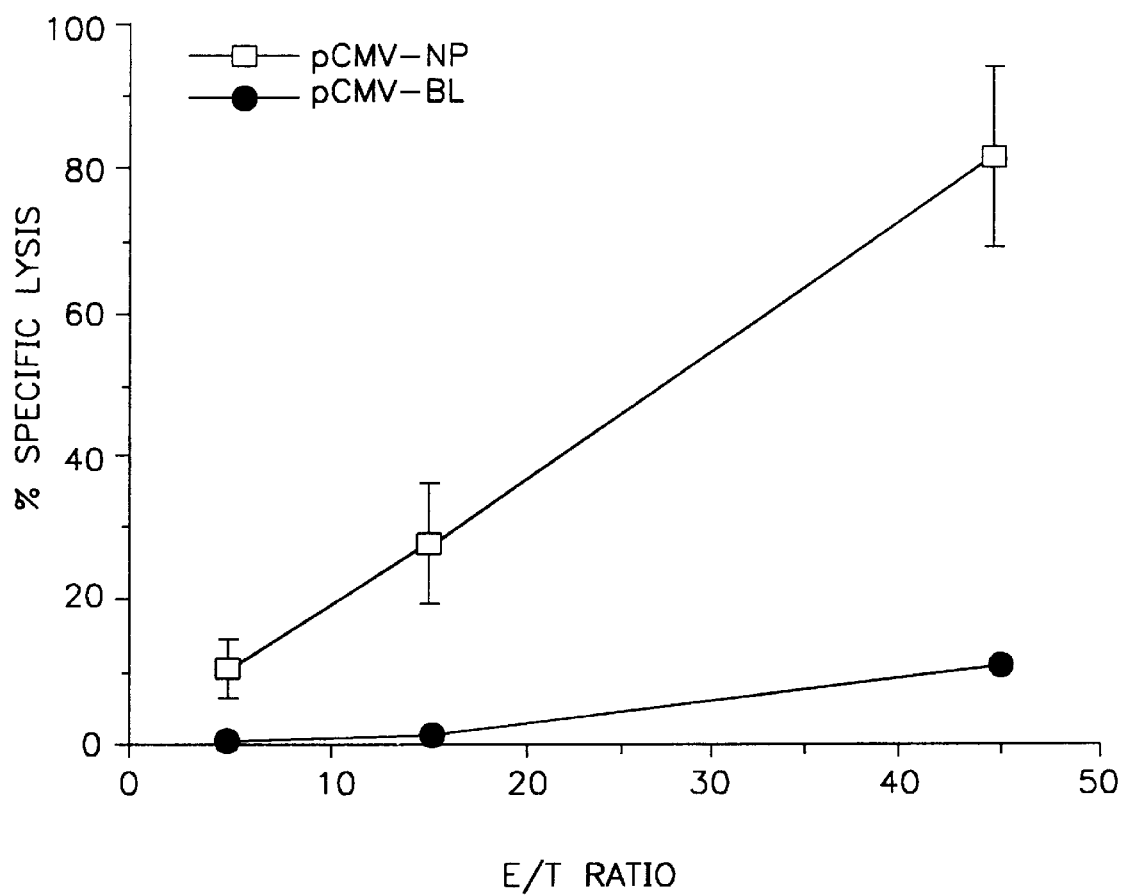
FIG. 26 depicts the results of an assay to detect antigen-specific cell lysis by T lymphocytes from mice immunized by epidermal administration of pCMV-NP plasmid.
Figure 27:
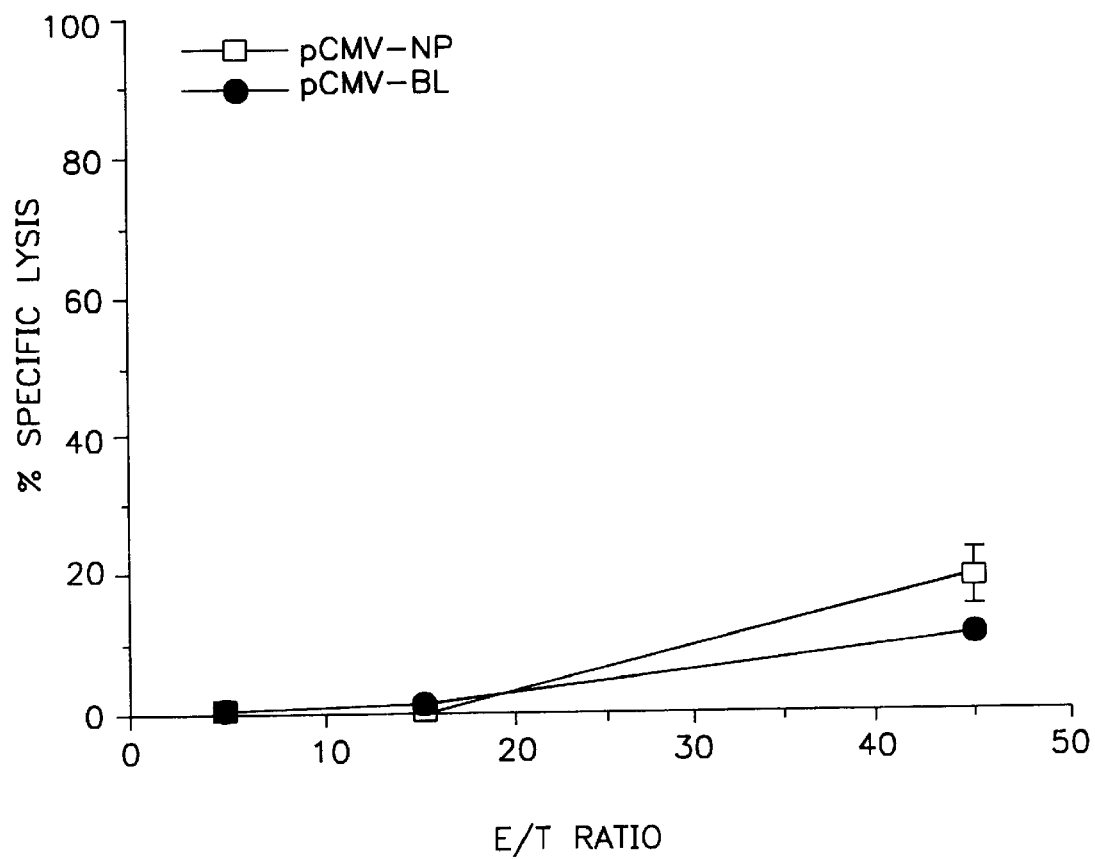
FIG. 27 depicts the results of an assay to detect antigen-specific cell lysis by T lymphocytes from the mice described in FIG. 26 in absence of pulsing of the cells with the antigen.

As shown in FIG. 26, mixed lymphocyte cultures prepared from the pCMV-NP injected animals displayed high levels of specific anti-NP cytolytic activity, reaching 10%, 30% and 80% of specific lysis at an effector to target (E/T) ratio of 5:1, 15:1 and 45:1, respectively. Control mice only displayed 1%, 1% and 9% under the same conditions. Further, in absense of exposure to the H-2$^d$ epitope peptide, there were not significant differences in CTL activity in the pCMV-NP injected and control mice (FIG. 27). These data indicate selective activation of TH1 cells in the pCMV-NP injected mice.

We claim:

1. A method for immunizing a host against an allergenic antigen comprising:

administering a naked polynucleotide to the skin or mucosa of the host, wherein the skin and mucosa have a high concentration of resident antigen presenting cells relative to other host tissues, wherein the naked polynucleotide operatively encodes for the allergenic antigen or allergenic antigen epitope; and, wherein the allergenic antigen is expressed in the antigen presenting cells without substantial secretion therefrom and preferentially activates Th1 lymphocytes while reducing antigen-stimulated IgE production in the host as compared to immunization of the host with a non-recombinant form of the allergenic antigen.

2. The method according to claim 1 wherein the naked polynucleotide is coated onto the tynes of a multiple tyne device and is administered by penetrating the skin or mucosa of the host with the tynes.

3. A method according to claim 1 wherein the antigen is not secreted by the antigen presenting cells.

4. The method according to claim 1 wherein the naked polynucleotide is under the control of a nuclear receptor promoter.

5. A method according to claim 4 wherein he promoter is activated by application of an activating ligand specific for the nuclear receptor to the skin of the host at the point of entry of the polynucleotide.

6. A method according to claim 5 wherein the ligand is selected from the group consisting of 1,25-dihydroxyvitamin $D_3$, steroid hormones, thyroid hormone and retinoids.

7. The method according to claim 1 wherein the host is reimmunized at least once with the allergenic antigen-encoding naked polynucleotide.

8. The method according to claim 1 wherein the host is reimmunized at least once with the allergenic antigen.

9. A method for immunizing a host against more than one allergenic antigen comprising:

administering a naked polynucleotide to the skin or mucosa of the host, wherein the skin and mucosa have a high concentration of resident antigen presenting cells relative to other host tissues, wherein the naked polynucleotides operatively encode for more than one allergenic antigen or allergenic antigen epitope; and, wherein the allergenic antigens are expressed in the antigen presenting cells without substantial secretion therefrom and preferentially activate Th1 lymphocytes while reducing antigen-stimulated IgE production in the host as compared to immunization of the host with a non-recombinant form of the allergenic antigens.

10. The method according to claim 1 wherein the naked polynucleotides are coated onto separate tynes of a multiple tyne device and are administered by penetrating the skin or mucosa of the host with the tynes.

* * * * *

UNITED STATES PATENT AND TRADEMARK OFFICE
CERTIFICATE OF CORRECTION

PATENT NO.     : 5,804,566

DATED          : 09/08/98

INVENTOR(S)    : Carson, et al.

It is certified that error appears in the above-identified patent and that said Letters Patent is hereby corrected as shown below:

In Column 33, the claims should read as follows:

1. A method for immunizing a host against an allergenic antigen comprising:

administering a naked polynucleotide to the skin of the host, wherein the skin has a high concentration of resident antigen presenting cells relative to other host tissues, wherein the naked polynucleotide operatively encodes for the allergenic antigen or allergenic antigen epitope; and, wherein the allergenic antigen is expressed in the antigen presenting cells without substantial secretion therefrom and preferentially activates Th1 lymphocytes while reducing antigen-stimulated IgE production in the host as compared to immunization of the host with a non-recombinant form of the allergenic antigen.

2. The method according to Claim 1 wherein the naked polynucleotide is coated onto the tynes of a multiple tyne device and is administered by penetrating the skin of the host with the tynes.

3. The method according to Claim 1 wherein the antigen is not secreted by the antigen presenting cells.

4. The method according to Claim 1 wherein the naked polynucleotide is under the control of a nuclear receptor promoter.

5. The method according to Claim 4 wherein the promoter is activated by application of an activating ligand specific for the nuclear receptor to the skin of the host at the point of entry of the polynucleotide.

6. The method according to Claim 5 wherein the ligand is selected from the group consisting of 1,25-dihydroxyvitamin $D_3$, steroid hormones, thyroid hormone and retinoids.

UNITED STATES PATENT AND TRADEMARK OFFICE
CERTIFICATE OF CORRECTION

PATENT NO. : 5,804,566

DATED : 09/08/98

INVENTOR(S) : Carson, et al.

It is certified that error appears in the above-identified patent and that said Letters Patent is hereby corrected as shown below:

In Column 34, the claims should read as follows:

7. The method according to Claim 1 wherein the host is reimmunized at least once with the allergenic antigen-encoding naked polynucleotide.

9. A method for immunizing a host against more than one allergenic antigen comprising:

administering a naked polynucleotide to the skin of the host, wherein the skin has a high concentration of resident antigen presenting cells relative to other host tissues, wherein the naked polynucleotides operatively encode for more than one allergenic antigen or allergenic antigen epitope; and, wherein the allergenic antigens are expressed in the antigen presenting cells without substantial secretion therefrom and preferentially activate Th1 lymphocytes while reducing antigen-stimulated IgE production in the host as compared to immunization of the host with a non-recombinant form of the allergenic antigens.

10. The method according to Claim 9 wherein the naked polynucleotides are coated onto separate tynes of a multiple tyne device and are administered by penetrating the skin of the host with the tynes.

UNITED STATES PATENT AND TRADEMARK OFFICE
CERTIFICATE OF CORRECTION

PATENT NO.     : 5,804,566

DATED          : 09/08/98

INVENTOR(S)    : Carson, et al.

It is certified that error appears in the above-identified patent and that said Letters Patent is hereby corrected as shown below:

In Column 34, the claims should read as follows:

11. A method for immunizing a host against an allergenic antigen comprising:

administering a naked polynucleotide to the mucosa of the host, wherein the mucosa has a high concentration of resident antigen presenting cells relative to other host tissues, wherein the naked polynucleotide operatively encodes for the allergenic antigen or allergenic antigen epitope; and, wherein the allergenic antigen is expressed in the antigen presenting cells without substantial secretion therefrom and preferentially activates Th1 lymphocytes while reducing antigen-stimulated IgE production in the host as compared to immunization of the host with a non-recombinant form of the allergenic antigen.

12. The method according to Claim 11 wherein the naked polynucleotide is under the control of a nuclear receptor promoter.

13. The method according to Claim 12 wherein the promoter is activated by application of an activating ligand specific for the nuclear receptor to the mucosa of the host at the point of entry of the polynucleotide.

14. The method according to Claim 13 wherein the ligand is selected from the group consisting of 1,25-dihydroxyvitamin $D_3$, steroid hormones, thyroid hormone and retinoids.

15. The method according to Claim 11 wherein the host is reimmunized at least once with the allergenic antigen-encoding naked polynucleotide.

UNITED STATES PATENT AND TRADEMARK OFFICE
CERTIFICATE OF CORRECTION

PATENT NO.    : 5,804,566

DATED         : 09/08/98

INVENTOR(S)   : Carson, et al.

It is certified that error appears in the above-identified patent and that said Letters Patent is hereby corrected as shown below:

In Column 34, the claims should read as follows:

16. The method according to Claim 11 wherein the host is reimmunized at least once with the allergenic antigen.

17. A method for immunizing a host against more than one allergenic antigen comprising:

administering a naked polynucleotide to the mucosa of the host, wherein the mucosa has a high concentration of resident antigen presenting cells relative to other host tissues, wherein the naked polynucleotides operatively encode for more than one allergenic antigen or allergenic antigen epitope; and, wherein the allergenic antigens are expressed in the antigen presenting cells without substantial secretion therefrom and preferentially activate Th1 lymphocytes while reducing antigen-stimulated IgE production in the host as compared to immunization of the host with a non-recombinant form of the allergenic antigens.

18. The method according to Claim 17 wherein the naked polynucleotides are coated onto separate tynes of a multiple tyne device and are administered by penetrating the mucosa of the host with the tynes.

Signed and Sealed this

Twenty-first Day of September, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO. : 5,804,566
DATED : September 8, 1998
INVENTOR(S) : Carson et al.

It is certified that error appears in the above-identified patent and that said Letters Patent is hereby corrected as shown below:

On the title page,

Please delete the Related U.S. Application Data [63] in its entirety and replace with:

-- Continuation-in-part of PCT Application No. US94/09661, filed August 25, 1994, which is a continuation-in-part of Ser. No. 112, 440, filed August 26, 1993, abandoned. --

Signed and Sealed this

Twelfth Day of December, 2000

Attest:

Q. TODD DICKINSON

*Attesting Officer*       *Director of Patents and Trademarks*

UNITED STATES PATENT AND TRADEMARK OFFICE
Certificate

Patent No. 5,804,566

Patented: September 8, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Dennis A. Carson, Del Mar, CA; and Eyal Raz, San Diego, CA.

Signed and Sealed this Twenty-seventh Day of May 2003.

CHRISTINA CHAN
*Supervisory Patent Examiner*
Art Unit 1644